United States Patent
Andersen

(10) Patent No.: US 9,394,532 B2
(45) Date of Patent: *Jul. 19, 2016

(54) STABILIZATION OF ALPHA-AMYLASES TOWARDS CALCIUM DEPLETION AND ACIDIC PH

(71) Applicant: NOVOZYMES A/S, Bagsvaerd (DK)

(72) Inventor: Carsten Andersen, Vaerloese (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,667

(22) Filed: Jan. 25, 2016

(65) Prior Publication Data

US 2016/0137996 A1    May 19, 2016

Related U.S. Application Data

(62) Division of application No. 14/525,877, filed on Oct. 28, 2014, now Pat. No. 9,273,297, which is a division of application No. 13/518,962, filed as application No. PCT/EP2011/050074 on Jan. 4, 2011, now Pat. No. 8,900,848.

(60) Provisional application No. 61/362,536, filed on Jul. 8, 2010, provisional application No. 61/355,230, filed on Jun. 16, 2010, provisional application No. 61/354,817, filed on Jun. 15, 2010, provisional application No. 61/354,775, filed on Jun. 15, 2010, provisional application No. 61/333,930, filed on May 12, 2010, provisional application No. 61/304,092, filed on Feb. 12, 2010, provisional application No. 61/292,327, filed on Jan. 5, 2010, provisional application No. 61/292,324, filed on Jan. 5, 2010.

(30) Foreign Application Priority Data

Jan. 4, 2010 (EP) .................................... 10150062
Jan. 4, 2010 (EP) .................................... 10150063

(51) Int. Cl.

| C12N 9/12 | (2006.01) |
| C07K 1/00 | (2006.01) |
| C12P 7/06 | (2006.01) |
| C11D 3/386 | (2006.01) |
| C12N 9/28 | (2006.01) |
| C12P 19/14 | (2006.01) |
| C12P 19/02 | (2006.01) |

(52) U.S. Cl.
CPC .............. *C12N 9/2417* (2013.01); *C11D 3/386* (2013.01); *C11D 3/38681* (2013.01); *C12P 19/02* (2013.01); *C12P 19/14* (2013.01); *C12Y 302/01001* (2013.01)

(58) Field of Classification Search
CPC ...... C12N 9/2417; C12N 9/2414; C12P 9/04; C12P 7/14; C11D 3/386
See application file for complete search history.

(56) References Cited

U.S. PATENT DOCUMENTS

| 6,197,070 B1 | 3/2001 | Horner |
| 8,435,577 B2 | 5/2013 | Andersen |
| 2013/0071913 A1 | 3/2013 | Andersen |

FOREIGN PATENT DOCUMENTS

| EP | 1 022 334 B1 | 7/2000 |
| EP | 1065261 A1 | 1/2001 |
| WO | 95/26397 A1 | 10/1995 |
| WO | 96/23873 A1 | 8/1996 |
| WO | 97/32961 A2 | 9/1997 |
| WO | 00/60060 A2 | 10/2000 |
| WO | 01/66712 A2 | 9/2001 |
| WO | 02/10355 A2 | 2/2002 |
| WO | 03/083054 A2 | 10/2003 |
| WO | 2006/002643 A2 | 1/2006 |
| WO | 2006/066596 A2 | 6/2006 |
| WO | 2009/134670 A2 | 11/2009 |
| WO | 2010/074999 A1 | 7/2010 |

OTHER PUBLICATIONS

Brzozowski et al., Biochemistry, vol. 39, pp. 9099-9107 (2000).
Conrad et al., Eur. J. Biochem., vol. 230, pp. 481-490 (1995).
Liu et al., Curr. Microbiol., vol. 60, pp. 162-166 (2009).
MacGregor et al., Biochemica et Biophysica Acta, vol. 1546, pp. 1-20 (2000).
Machius et al., J. Mol. Biol., vol. 246, pp. 545-559 (1995).
Machius et al., Structure, vol. 6, pp. 281-292 (1998).
Marcel, UniProt Database, Accession No. Q03657 (1996).
Nielsen et al., Biochimica et Biophysica Acta, vol. 1543, pp. 255-265 (2000).
Nishizawa et al., DNA, vol. 6, pp. 255-265 (1987).
Nonaka et al., The Journal of Biological Chemistry, vol. 278, No. 27, pp. 24818-24824 (2003).
Priyadharshini et al., Biotechnol. Lett., vol. 29, pp. 1493-1499 (2007).
Richardson et al., The Journal of Biological Chemistry, vol. 277, No. 29, pp. 26501-26507 (2002).
Rodenburg et al., Eur. J. Biochem., vol. 221, pp. 277-284 (1994).
Suvd et al., J. Biochem., vol. 129, pp. 416-468 (2001).
Marcel, 1991, EMBL Access No. X60779.
Niakajima et al., 1985, J Bacteriol 163 (1), 401-406.

*Primary Examiner* — Maryam Monshipouri
(74) *Attorney, Agent, or Firm* — Michael W. Krenicky

(57) ABSTRACT

The present invention relates to variants of a parent alpha-amylase, the variant having improved stability or activity at low calcium conditions or at low pH.

14 Claims, No Drawings

SEQUENCE LISTING

```
<160> NUMBER OF SEQ ID NOS: 17

<210> SEQ ID NO 1
<211> LENGTH: 1458
<212> TYPE: DNA
<213> ORGANISM: Bacillus sp.
<220> FEATURE:
<221> NAME/KEY: CDS
<222> LOCATION: (1)..(1458)

<400> SEQUENCE: 1 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt      96
Leu Pro Asn Asp Gly Asn His Trp Asn Arg Leu Arg Ser Asp Ala Ser
                20                  25                  30 aac cta aaa gat aaa ggg atc tca gcg gtt tgg att cct cct gca tgg     144
Asn Leu Lys Asp Lys Gly Ile Ser Ala Val Trp Ile Pro Pro Ala Trp
            35                  40                  45 aag ggt gcc tct caa aat gat gtg ggg tat ggt gct tat gat ctg tat     192
Lys Gly Ala Ser Gln Asn Asp Val Gly Tyr Gly Ala Tyr Asp Leu Tyr
        50                  55                  60 gat tta gga gaa ttc aat caa aaa gga acc att cgt aca aaa tat gga     240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga     288
Thr Arg Asn Gln Leu Gln Ala Ala Val Asn Ala Leu Lys Ser Asn Gly
                85                  90                  95
```

-continued

| | |
|---|---|
| att caa gtg tat ggc gat gtt gta atg aat cat aaa ggg gga gca gac<br>Ile Gln Val Tyr Gly Asp Val Val Met Asn His Lys Gly Gly Ala Asp<br>100         105                 110 | 336 |
| gct acc gaa atg gtt agg gcg gtt gaa gta aac ccg aat aat aga aat<br>Ala Thr Glu Met Val Arg Ala Val Glu Val Asn Pro Asn Asn Arg Asn<br>    115                 120                 125 | 384 |
| caa gaa gtg tcc ggt gaa tat aca att gag gct tgg aca aag ttt gac<br>Gln Glu Val Ser Gly Glu Tyr Thr Ile Glu Ala Trp Thr Lys Phe Asp<br>130         135                 140 | 432 |
| ttt cct gga cga ggt aat acc cat tca aac ttc aaa tgg aga tgg tat<br>Phe Pro Gly Arg Gly Asn Thr His Ser Asn Phe Lys Trp Arg Trp Tyr<br>145             150                 155                 160 | 480 |
| cac ttt gat gga gta gat tgg gat cag tca cgt aag ctg aac aat cga<br>His Phe Asp Gly Val Asp Trp Asp Gln Ser Arg Lys Leu Asn Asn Arg<br>                165                 170                 175 | 528 |
| att tat aaa ttt aga ggt gat gga aaa ggg tgg gat tgg gaa gtc gat<br>Ile Tyr Lys Phe Arg Gly Asp Gly Lys Gly Trp Asp Trp Glu Val Asp<br>        180                 185                 190 | 576 |
| aca gaa aac ggt aac tat gat tac cta atg tat gca gat att gac atg<br>Thr Glu Asn Gly Asn Tyr Asp Tyr Leu Met Tyr Ala Asp Ile Asp Met<br>    195                 200                 205 | 624 |
| gat cac cca gag gta gtg aat gag cta aga aat tgg ggt gtt tgg tat<br>Asp His Pro Glu Val Val Asn Glu Leu Arg Asn Trp Gly Val Trp Tyr<br>210                 215                 220 | 672 |
| acg aat aca tta ggc ctt gat ggt ttt aga ata gat gca gta aaa cat<br>Thr Asn Thr Leu Gly Leu Asp Gly Phe Arg Ile Asp Ala Val Lys His<br>225                 230                 235                 240 | 720 |
| ata aaa tac agc ttt act cgt gat tgg atc aat cat gtt aga agt gca<br>Ile Lys Tyr Ser Phe Thr Arg Asp Trp Ile Asn His Val Arg Ser Ala<br>                245                 250                 255 | 768 |
| act ggc aaa aat atg ttt gcg gtt gcg gaa ttt tgg aaa aat gat tta<br>Thr Gly Lys Asn Met Phe Ala Val Ala Glu Phe Trp Lys Asn Asp Leu<br>        260                 265                 270 | 816 |
| ggt gct att gaa aac tat tta aac aaa aca aac tgg aac cat tca gtc<br>Gly Ala Ile Glu Asn Tyr Leu Asn Lys Thr Asn Trp Asn His Ser Val<br>    275                 280                 285 | 864 |
| ttt gat gtt ccg ctg cac tat aac ctc tat aat gct tca aaa agc gga<br>Phe Asp Val Pro Leu His Tyr Asn Leu Tyr Asn Ala Ser Lys Ser Gly<br>290                 295                 300 | 912 |
| ggg aat tat gat atg agg caa ata ttt aat ggt aca gtc gtg caa aga<br>Gly Asn Tyr Asp Met Arg Gln Ile Phe Asn Gly Thr Val Val Gln Arg<br>305                 310                 315                 320 | 960 |
| cat cca atg cat gct gtt aca ttt gtt gat aat cat gat tcg caa cct<br>His Pro Met His Ala Val Thr Phe Val Asp Asn His Asp Ser Gln Pro<br>                325                 330                 335 | 1008 |
| gaa gaa gct tta gag tct ttt gtt gaa gaa tgg ttc aaa cca tta gcg<br>Glu Glu Ala Leu Glu Ser Phe Val Glu Glu Trp Phe Lys Pro Leu Ala<br>        340                 345                 350 | 1056 |
| tat gct ttg aca tta aca cgt gaa caa ggc tac cct tct gta ttt tat<br>Tyr Ala Leu Thr Leu Thr Arg Glu Gln Gly Tyr Pro Ser Val Phe Tyr<br>    355                 360                 365 | 1104 |
| gga gat tat tat ggc att cca acg cat ggt gta cca gcg atg aaa tcg<br>Gly Asp Tyr Tyr Gly Ile Pro Thr His Gly Val Pro Ala Met Lys Ser<br>370                 375                 380 | 1152 |
| aaa att gac ccg att cta gaa gcg cgt caa aag tat gca tat gga aga<br>Lys Ile Asp Pro Ile Leu Glu Ala Arg Gln Lys Tyr Ala Tyr Gly Arg<br>385                 390                 395                 400 | 1200 |
| caa aat gac tac tta gac cat cat aat atc att ggt tgg aca cgt gaa<br>Gln Asn Asp Tyr Leu Asp His His Asn Ile Ile Gly Trp Thr Arg Glu<br>                405                 410                 415 | 1248 |

```
ggg aat aca gca cac ccc aac tct ggt tta gct act atc atg tcc gat     1296
Gly Asn Thr Ala His Pro Asn Ser Gly Leu Ala Thr Ile Met Ser Asp
            420                 425                 430 gga gca gga gga aat aag tgg atg ttt gtt ggg cgt aat aaa gct ggt     1344
Gly Ala Gly Gly Asn Lys Trp Met Phe Val Gly Arg Asn Lys Ala Gly
        435                 440                 445 caa gtt tgg acc gat atc act gga aat cgt gca ggt act gtt acg att     1392
Gln Val Trp Thr Asp Ile Thr Gly Asn Arg Ala Gly Thr Val Thr Ile
    450                 455                 460 aat gct gat gga tgg ggt aat ttt tct gta aat gga gga tca gtt tct     1440
Asn Ala Asp Gly Trp Gly Asn Phe Ser Val Asn Gly Gly Ser Val Ser
465                 470                 475                 480 att tgg gta aac aaa taa                                             1458
Ile Trp Val Asn Lys
                485
```

<210> SEQ ID NO 2
<211> LENGTH: 485
<212> TYPE: PRT
<213> ORGANISM: Bacillus sp.

<400> SEQUENCE: 2

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270
```

```
Gly Ala Ile Glu Asn Tyr Leu Asn Lys Thr Asn Trp Asn His Ser Val
            275                 280                 285
Phe Asp Val Pro Leu His Tyr Asn Leu Tyr Asn Ala Ser Lys Ser Gly
        290                 295                 300
Gly Asn Tyr Asp Met Arg Gln Ile Phe Asn Gly Thr Val Val Gln Arg
305                 310                 315                 320
His Pro Met His Ala Val Thr Phe Val Asp Asn His Asp Ser Gln Pro
                325                 330                 335
Glu Glu Ala Leu Glu Ser Phe Val Glu Trp Phe Lys Pro Leu Ala
            340                 345                 350
Tyr Ala Leu Thr Leu Thr Arg Glu Gln Gly Tyr Pro Ser Val Phe Tyr
        355                 360                 365
Gly Asp Tyr Tyr Gly Ile Pro Thr His Gly Val Pro Ala Met Lys Ser
370                 375                 380
Lys Ile Asp Pro Ile Leu Glu Ala Arg Gln Lys Tyr Ala Tyr Gly Arg
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
            420                 425                 430
Gly Ala Gly Gly Asn Lys Trp Met Phe Val Gly Arg Asn Lys Ala Gly
        435                 440                 445
Gln Val Trp Thr Asp Ile Thr Gly Asn Arg Ala Gly Thr Val Thr Ile
    450                 455                 460
Asn Ala Asp Gly Trp Gly Asn Phe Ser Val Asn Gly Gly Ser Val Ser
465                 470                 475                 480
Ile Trp Val Asn Lys
                485

<210> SEQ ID NO 3
<211> LENGTH: 1452
<212> TYPE: DNA
<213> ORGANISM: Bacillus licheniformis
<220> FEATURE:
<221> NAME/KEY: CDS
<222> LOCATION: (1)..(1452)

<400> SEQUENCE: 3 gca aat ctt aat ggg acg ctg atg cag tat ttt gaa tgg tac atg ccc       48
Ala Asn Leu Asn Gly Thr Leu Met Gln Tyr Phe Glu Trp Tyr Met Pro
1               5                   10                  15 aat gac ggc caa cat tgg agg cgt ttg caa aac gac tcg gca tat ttg       96
Asn Asp Gly Gln His Trp Arg Arg Leu Gln Asn Asp Ser Ala Tyr Leu
            20                  25                  30 gct gaa cac ggt att act gcc gtc tgg att ccc ccg gca tat aag gga      144
Ala Glu His Gly Ile Thr Ala Val Trp Ile Pro Pro Ala Tyr Lys Gly
        35                  40                  45 acg agc caa gcg gat gtg ggc tac ggt gct tac gac ctt tat gat tta      192
Thr Ser Gln Ala Asp Val Gly Tyr Gly Ala Tyr Asp Leu Tyr Asp Leu
    50                  55                  60 ggg gag ttt cat caa aaa ggg acg gtt cgg aca aag tac ggc aca aaa      240
Gly Glu Phe His Gln Lys Gly Thr Val Arg Thr Lys Tyr Gly Thr Lys
65                  70                  75                  80 gga gag ctg caa tct gcg atc aaa agt ctt cat tcc cgc gac att aac      288
Gly Glu Leu Gln Ser Ala Ile Lys Ser Leu His Ser Arg Asp Ile Asn
                85                  90                  95
```

```
gtt tac ggg gat gtg gtc atc aac cac aaa ggc ggc gct gat gcg acc      336
Val Tyr Gly Asp Val Val Ile Asn His Lys Gly Gly Ala Asp Ala Thr
            100                 105                 110 gaa gat gta acc gcg gtt gaa gtc gat ccc gct gac cgc aac cgc gta      384
Glu Asp Val Thr Ala Val Glu Val Asp Pro Ala Asp Arg Asn Arg Val
        115                 120                 125 att tca gga gaa cac cta att aaa gcc tgg aca cat ttt cat ttt ccg      432
Ile Ser Gly Glu His Leu Ile Lys Ala Trp Thr His Phe His Phe Pro
    130                 135                 140 ggg cgc ggc agc aca tac agc gat ttt aaa tgg cat tgg tac cat ttt      480
Gly Arg Gly Ser Thr Tyr Ser Asp Phe Lys Trp His Trp Tyr His Phe
145                 150                 155                 160 gac gga acc gat tgg gac gag tcc cga aag ctg aac cgc atc tat aag      528
Asp Gly Thr Asp Trp Asp Glu Ser Arg Lys Leu Asn Arg Ile Tyr Lys
                165                 170                 175 ttt caa gga aag gct tgg gat tgg gaa gtt tcc aat gaa aac ggc aac      576
Phe Gln Gly Lys Ala Trp Asp Trp Glu Val Ser Asn Glu Asn Gly Asn
            180                 185                 190 tat gat tat ttg atg tat gcc gac atc gat tat gac cat cct gat gtc      624
Tyr Asp Tyr Leu Met Tyr Ala Asp Ile Asp Tyr Asp His Pro Asp Val
        195                 200                 205 gca gca gaa att aag aga tgg ggc act tgg tat gcc aat gaa ctg caa      672
Ala Ala Glu Ile Lys Arg Trp Gly Thr Trp Tyr Ala Asn Glu Leu Gln
    210                 215                 220 ttg gac ggt ttc cgt ctt gat gct gtc aaa cac att aaa ttt tct ttt      720
Leu Asp Gly Phe Arg Leu Asp Ala Val Lys His Ile Lys Phe Ser Phe
225                 230                 235                 240 ttg cgg gat tgg gtt aat cat gtc agg gaa aaa acg ggg aag gaa atg      768
Leu Arg Asp Trp Val Asn His Val Arg Glu Lys Thr Gly Lys Glu Met
                245                 250                 255 ttt acg gta gct gaa tat tgg cag aat gac ttg ggc gcg ctg gaa aac      816
Phe Thr Val Ala Glu Tyr Trp Gln Asn Asp Leu Gly Ala Leu Glu Asn
            260                 265                 270 tat ttg aac aaa aca aat ttt aat cat tca gtg ttt gac gtg ccg ctt      864
Tyr Leu Asn Lys Thr Asn Phe Asn His Ser Val Phe Asp Val Pro Leu
        275                 280                 285 cat tat cag ttc cat gct gca tcg aca cag gga ggc ggc tat gat atg      912
His Tyr Gln Phe His Ala Ala Ser Thr Gln Gly Gly Gly Tyr Asp Met
    290                 295                 300 agg aaa ttg ctg aac ggt acg gtc gtt tcc aag cat ccg ttg aaa tcg      960
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag     1008
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc     1056
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg     1104
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att     1152
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat     1200
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac     1248
Asp Tyr Phe Asp His His Asp Ile Val Gly Trp Thr Arg Glu Gly Asp
                405                 410                 415
```

```
agc tcg gtt gca aat tca ggt ttg gcg gca tta ata aca gac gga ccc    1296
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca    1344
Gly Gly Ala Lys Arg Met Tyr Val Gly Arg Gln Asn Ala Gly Glu Thr
            435                 440                 445 tgg cat gac att acc gga aac cgt tcg gag ccg gtt gtc atc aat tcg    1392
Trp His Asp Ile Thr Gly Asn Arg Ser Glu Pro Val Val Ile Asn Ser
450                 455                 460 gaa ggc tgg gga gag ttt cac gta aac ggc ggg tcg gtt tca att tat    1440
Glu Gly Trp Gly Glu Phe His Val Asn Gly Gly Ser Val Ser Ile Tyr
465                 470                 475                 480 gtt caa aga tag                                                    1452
Val Gln Arg <210> SEQ ID NO 4
<211> LENGTH: 483
<212> TYPE: PRT
<213> ORGANISM: Bacillus licheniformis

<400> SEQUENCE: 4

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270
```

```
Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
        290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 5
<211> LENGTH: 1452
<212> TYPE: DNA
<213> ORGANISM: Bacillus amyloliquefaciens
<220> FEATURE:
<221> NAME/KEY: CDS
<222> LOCATION: (1)..(1452)

<400> SEQUENCE: 5 gta aat ggc acg ctg atg cag tat ttt gaa tgg tat acg ccg aac gac    48
Val Asn Gly Thr Leu Met Gln Tyr Phe Glu Trp Tyr Thr Pro Asn Asp
1               5                  10                  15 ggc cag cat tgg aaa cga ttg cag aat gat gcg gaa cat tta tcg gat    96
Gly Gln His Trp Lys Arg Leu Gln Asn Asp Ala Glu His Leu Ser Asp
            20                  25                  30 atc gga atc act gcc gtc tgg att cct ccc gca tac aaa gga ttg agc   144
Ile Gly Ile Thr Ala Val Trp Ile Pro Pro Ala Tyr Lys Gly Leu Ser
        35                  40                  45 caa tcc gat aac gga tac gga cct tat gat ttg tat gat tta gga gaa   192
Gln Ser Asp Asn Gly Tyr Gly Pro Tyr Asp Leu Tyr Asp Leu Gly Glu
    50                  55                  60 ttc cag caa aaa ggg acg gtc aga acg aaa tac ggc aca aaa tca gag   240
Phe Gln Gln Lys Gly Thr Val Arg Thr Lys Tyr Gly Thr Lys Ser Glu
65                  70                  75                  80 ctt caa gat gcg atc ggc tca ctg cat tcc cgg aac gtc caa gta tac   288
Leu Gln Asp Ala Ile Gly Ser Leu His Ser Arg Asn Val Gln Val Tyr
                85                  90                  95 gga gat gtg gtt ttg aat cat aag gct ggt gct gat gca aca gaa gat   336
Gly Asp Val Val Leu Asn His Lys Ala Gly Ala Asp Ala Thr Glu Asp
            100                 105                 110
```

```
gta act gcc gtc gaa gtc aat ccg gcc aat aga aat cag gaa act tcg        384
Val Thr Ala Val Glu Val Asn Pro Ala Asn Arg Asn Gln Glu Thr Ser
        115             120                 125 gag gaa tat caa atc aaa gcg tgg acg gat ttt cgt ttt ccg ggc cgt        432
Glu Glu Tyr Gln Ile Lys Ala Trp Thr Asp Phe Arg Phe Pro Gly Arg
        130             135                 140 gga aac acg tac agt gat ttt aaa tgg cat tgg tat cat ttc gac gga        480
Gly Asn Thr Tyr Ser Asp Phe Lys Trp His Trp Tyr His Phe Asp Gly
145             150                 155                 160 gcg gac tgg gat gaa tcc cgg aag atc agc cgc atc ttt aag ttt cgt        528
Ala Asp Trp Asp Glu Ser Arg Lys Ile Ser Arg Ile Phe Lys Phe Arg
                165                 170                 175 ggg gaa gga aaa gcg tgg gat tgg gaa gta tca agt gaa aac ggc aac        576
Gly Glu Gly Lys Ala Trp Asp Trp Glu Val Ser Ser Glu Asn Gly Asn
        180                 185                 190 tat gac tat tta atg tat gct gat gtt gac tac gac cac cct gat gtc        624
Tyr Asp Tyr Leu Met Tyr Ala Asp Val Asp Tyr Asp His Pro Asp Val
            195                 200                 205 gtg gca gag aca aaa aaa tgg ggt atc tgg tat gcg aat gaa ctg tca        672
Val Ala Glu Thr Lys Lys Trp Gly Ile Trp Tyr Ala Asn Glu Leu Ser
210             215                 220 tta gac ggc ttc cgt att gat gcc gcc aaa cat att aaa ttt tca ttt        720
Leu Asp Gly Phe Arg Ile Asp Ala Ala Lys His Ile Lys Phe Ser Phe
225             230                 235                 240 ctg cgt gat tgg gtt cag gcg gtc aga cag gcg acg gga aaa gaa atg        768
Leu Arg Asp Trp Val Gln Ala Val Arg Gln Ala Thr Gly Lys Glu Met
                245                 250                 255 ttt acg gtt gcg gag tat tgg cag aat aat gcc ggg aaa ctc gaa aac        816
Phe Thr Val Ala Glu Tyr Trp Gln Asn Asn Ala Gly Lys Leu Glu Asn
        260                 265                 270 tac ttg aat aaa aca agc ttt aat caa tcc gtg ttt gat gtt ccg ctt        864
Tyr Leu Asn Lys Thr Ser Phe Asn Gln Ser Val Phe Asp Val Pro Leu
            275                 280                 285 cat ttc aat tta cag gcg gct tcc tca caa gga ggc gga tat gat atg        912
His Phe Asn Leu Gln Ala Ala Ser Ser Gln Gly Gly Gly Tyr Asp Met
        290                 295                 300 agg cgt ttg ctg gac ggt acc gtt gtg tcc agg cat ccg gaa aag gcg        960
Arg Arg Leu Leu Asp Gly Thr Val Val Ser Arg His Pro Glu Lys Ala
305             310                 315                 320 gtt aca ttt gtt gaa aat cat gac aca cag ccg gga cag tca ttg gaa       1008
Val Thr Phe Val Glu Asn His Asp Thr Gln Pro Gly Gln Ser Leu Glu
                325                 330                 335 tcg aca gtc caa act tgg ttt aaa ccg ctt gca tac gcc ttt att ttg       1056
Ser Thr Val Gln Thr Trp Phe Lys Pro Leu Ala Tyr Ala Phe Ile Leu
        340                 345                 350 aca aga gaa tcc ggt tat cct cag gtg ttc tat ggg gat atg tac ggg       1104
Thr Arg Glu Ser Gly Tyr Pro Gln Val Phe Tyr Gly Asp Met Tyr Gly
            355                 360                 365 aca aaa ggg aca tcg cca aag gaa att ccc tca ctg aaa gat aat ata       1152
Thr Lys Gly Thr Ser Pro Lys Glu Ile Pro Ser Leu Lys Asp Asn Ile
        370                 375                 380 gag ccg att tta aaa gcg cgt aag gag tac gca tac ggg ccc cag cac       1200
Glu Pro Ile Leu Lys Ala Arg Lys Glu Tyr Ala Tyr Gly Pro Gln His
385             390                 395                 400 gat tat att gac cac ccg gat gtg atc gga tgg acg agg gaa ggt gac       1248
Asp Tyr Ile Asp His Pro Asp Val Ile Gly Trp Thr Arg Glu Gly Asp
                405                 410                 415 agc tcc gcc gcc aaa tca ggt ttg gcc gct tta atc acg gac gga ccc       1296
Ser Ser Ala Ala Lys Ser Gly Leu Ala Ala Leu Ile Thr Asp Gly Pro
        420                 425                 430
```

```
ggc gga tca aag cgg atg tat gcc ggc ctg aaa aat gcc ggc gag aca    1344
Gly Gly Ser Lys Arg Met Tyr Ala Gly Leu Lys Asn Ala Gly Glu Thr
        435                 440                 445 tgg tat gac ata acg ggc aac cgt tca gat act gta aaa atc gga tct    1392
Trp Tyr Asp Ile Thr Gly Asn Arg Ser Asp Thr Val Lys Ile Gly Ser
450                 455                 460 gac ggc tgg gga gag ttt cat gta aac gat ggg tcc gtc tcc att tat    1440
Asp Gly Trp Gly Glu Phe His Val Asn Asp Gly Ser Val Ser Ile Tyr
465                 470                 475                 480 gtt cag aaa taa                                                    1452
Val Gln Lys
```

<210> SEQ ID NO 6
<211> LENGTH: 483
<212> TYPE: PRT
<213> ORGANISM: Bacillus amyloliquefaciens

<400> SEQUENCE: 6

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300
```

-continued

```
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 7
<211> LENGTH: 1548
<212> TYPE: DNA
<213> ORGANISM: Bacillus stearothermophilus
<220> FEATURE:
<221> NAME/KEY: CDS
<222> LOCATION: (1)..(1548)

<400> SEQUENCE: 7 gcc gca ccg ttt aac ggc acc atg atg cag tat ttt gaa tgg tac ttg     48
Ala Ala Pro Phe Asn Gly Thr Met Met Gln Tyr Phe Glu Trp Tyr Leu
1               5                   10                  15 ccg gat gat ggc acg tta tgg acc aaa gtg gcc aat gaa gcc aac aac     96
Pro Asp Asp Gly Thr Leu Trp Thr Lys Val Ala Asn Glu Ala Asn Asn
            20                  25                  30 tta tcc agc ctt ggc atc acc gct ctt tgg ctg ccg ccc gct tac aaa    144
Leu Ser Ser Leu Gly Ile Thr Ala Leu Trp Leu Pro Pro Ala Tyr Lys
        35                  40                  45 gga aca agc cgc agc gac gta ggg tac gga gta tac gac ttg tat gac    192
Gly Thr Ser Arg Ser Asp Val Gly Tyr Gly Val Tyr Asp Leu Tyr Asp
    50                  55                  60 ctc ggc gaa ttc aat caa aaa ggg acc gtc cgc aca aaa tac gga aca    240
Leu Gly Glu Phe Asn Gln Lys Gly Thr Val Arg Thr Lys Tyr Gly Thr
65                  70                  75                  80 aaa gct caa tat ctt caa gcc att caa gcc gcc cac gcc gct gga atg    288
Lys Ala Gln Tyr Leu Gln Ala Ile Gln Ala Ala His Ala Ala Gly Met
                85                  90                  95 caa gtg tac gcc gat gtc gtg ttc gac cat aaa ggc ggc gct gac ggc    336
Gln Val Tyr Ala Asp Val Val Phe Asp His Lys Gly Gly Ala Asp Gly
            100                 105                 110 acg gaa tgg gtg gac gcc gtc gaa gtc aat ccg tcc gac cgc aac caa    384
Thr Glu Trp Val Asp Ala Val Glu Val Asn Pro Ser Asp Arg Asn Gln
        115                 120                 125
```

| | | |
|---|---|---|
| gaa atc tcg ggc acc tat caa atc caa gca tgg acg aaa ttt gat ttt<br>Glu Ile Ser Gly Thr Tyr Gln Ile Gln Ala Trp Thr Lys Phe Asp Phe<br>130               135                   140 | | 432 |
| ccc ggg cgg ggc aac acc tac tcc agc ttt aag tgg cgc tgg tac cat<br>Pro Gly Arg Gly Asn Thr Tyr Ser Ser Phe Lys Trp Arg Trp Tyr His<br>145               150               155              160 | | 480 |
| ttt gac ggc gtt gat tgg gac gaa agc cga aaa ttg agc cgc att tac<br>Phe Asp Gly Val Asp Trp Asp Glu Ser Arg Lys Leu Ser Arg Ile Tyr<br>                   165               170               175 | | 528 |
| aaa ttc cgc ggc atc ggc aaa gcg tgg gat tgg gaa gta gac acg gaa<br>Lys Phe Arg Gly Ile Gly Lys Ala Trp Asp Trp Glu Val Asp Thr Glu<br>             180               185               190 | | 576 |
| aac gga aac tat gac tac tta atg tat gcc gac ctt gat atg gat cat<br>Asn Gly Asn Tyr Asp Tyr Leu Met Tyr Ala Asp Leu Asp Met Asp His<br>                   195               200               205 | | 624 |
| ccc gaa gtc gtg acc gag ctg aaa aac tgg ggg aaa tgg tat gtc aac<br>Pro Glu Val Val Thr Glu Leu Lys Asn Trp Gly Lys Trp Tyr Val Asn<br>210               215                   220 | | 672 |
| aca acg aac att gat ggg ttc cgg ctt gat gcc gtc aag cat att aag<br>Thr Thr Asn Ile Asp Gly Phe Arg Leu Asp Ala Val Lys His Ile Lys<br>225               230               235              240 | | 720 |
| ttc agt ttt ttt cct gat tgg ttg tcg tat gtg cgt tct cag act ggc<br>Phe Ser Phe Phe Pro Asp Trp Leu Ser Tyr Val Arg Ser Gln Thr Gly<br>                   245               250               255 | | 768 |
| aag ccg cta ttt acc gtc ggg gaa tat tgg agc tat gac atc aac aag<br>Lys Pro Leu Phe Thr Val Gly Glu Tyr Trp Ser Tyr Asp Ile Asn Lys<br>             260               265               270 | | 816 |
| ttg cac aat tac att acg aaa aca gac gga acg atg tct ttg ttt gat<br>Leu His Asn Tyr Ile Thr Lys Thr Asp Gly Thr Met Ser Leu Phe Asp<br>                   275               280               285 | | 864 |
| gcc ccg tta cac aac aaa ttt tat acc gct tcc aaa tca ggg ggc gca<br>Ala Pro Leu His Asn Lys Phe Tyr Thr Ala Ser Lys Ser Gly Gly Ala<br>290               295                   300 | | 912 |
| ttt gat atg cgc acg tta atg acc aat act ctc atg aaa gat caa ccg<br>Phe Asp Met Arg Thr Leu Met Thr Asn Thr Leu Met Lys Asp Gln Pro<br>305               310               315              320 | | 960 |
| aca ttg gcc gtc acc ttc gtt gat aat cat gac acc gaa ccc ggc caa<br>Thr Leu Ala Val Thr Phe Val Asp Asn His Asp Thr Glu Pro Gly Gln<br>                   325               330               335 | | 1008 |
| gcg ctg cag tca tgg gtc gac cca tgg ttc aaa ccg ttg gct tac gcc<br>Ala Leu Gln Ser Trp Val Asp Pro Trp Phe Lys Pro Leu Ala Tyr Ala<br>             340               345               350 | | 1056 |
| ttt att cta act cgg cag gaa gga tac ccg tgc gtc ttt tat ggt gac<br>Phe Ile Leu Thr Arg Gln Glu Gly Tyr Pro Cys Val Phe Tyr Gly Asp<br>                   355               360               365 | | 1104 |
| tat tat ggc att cca caa tat aac att cct tcg ctg aaa agc aaa atc<br>Tyr Tyr Gly Ile Pro Gln Tyr Asn Ile Pro Ser Leu Lys Ser Lys Ile<br>370               375                   380 | | 1152 |
| gat ccg ctc ctc atc gcg cgc agg gat tat gct tac gga acg caa cat<br>Asp Pro Leu Leu Ile Ala Arg Arg Asp Tyr Ala Tyr Gly Thr Gln His<br>385               390               395              400 | | 1200 |
| gat tat ctt gat cac tcc gac atc atc ggg tgg aca agg gaa ggg ggc<br>Asp Tyr Leu Asp His Ser Asp Ile Ile Gly Trp Thr Arg Glu Gly Gly<br>                   405               410               415 | | 1248 |
| act gaa aaa cca gga tcc gga ctg gcc gca ctg atc acc gat ggg ccg<br>Thr Glu Lys Pro Gly Ser Gly Leu Ala Ala Leu Ile Thr Asp Gly Pro<br>             420               425               430 | | 1296 |
| gga gga agc aaa tgg atg tac gtt ggc aaa caa cac gct gga aaa gtg<br>Gly Gly Ser Lys Trp Met Tyr Val Gly Lys Gln His Ala Gly Lys Val<br>             435               440               445 | | 1344 |

```
ttc tat gac ctt acc ggc aac cgg agt gac acc gtc acc atc aac agt    1392
Phe Tyr Asp Leu Thr Gly Asn Arg Ser Asp Thr Val Thr Ile Asn Ser
    450                 455                 460 gat gga tgg ggg gaa ttc aaa gtc aat ggc ggt tcg gtt tcg gtt tgg    1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc    1488
Val Pro Arg Lys Thr Thr Val Ser Thr Ile Ala Arg Pro Ile Thr Thr
                485                 490                 495 cga ccg tgg act ggt gaa ttc gtc cgt tgg acc gaa cca cgg ttg gtg    1536
Arg Pro Trp Thr Gly Glu Phe Val Arg Trp Thr Glu Pro Arg Leu Val
            500                 505                 510 gca tgg cct tga                                                     1548
Ala Trp Pro
        515

<210> SEQ ID NO 8
<211> LENGTH: 515
<212> TYPE: PRT
<213> ORGANISM: Bacillus stearothermophilus

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270
```

```
Leu His Asn Tyr Ile Thr Lys Thr Asp Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
       515

<210> SEQ ID NO 9
<211> LENGTH: 492
<212> TYPE: PRT
<213> ORGANISM: Bacillus circulans

<400> SEQUENCE: 9

Lys Arg Asn His Thr Met Met Gln Phe Phe Glu Trp His Leu Ala Ala
1               5                   10                  15

Asp Gly Asp His Trp Lys Arg Leu Ala Glu Met Ala Pro Glu Leu Lys
                20                  25                  30

Ala Lys Gly Ile Asp Thr Val Trp Val Pro Pro Val Thr Lys Ala Val
            35                  40                  45

Ser Ala Glu Asp Thr Gly Tyr Gly Val Tyr Asp Leu Tyr Asp Leu Gly
        50                  55                  60

Glu Phe Asp Gln Lys Gly Thr Val Arg Thr Lys Tyr Gly Thr Lys Gln
65                  70                  75                  80

Glu Leu Ile Glu Ala Ile Ala Glu Cys Gln Lys Asn Gly Ile Ala Val
                85                  90                  95

Tyr Val Asp Leu Val Met Asn His Lys Ala Gly Ala Asp Glu Thr Glu
            100                 105                 110
```

Val Phe Lys Val Ile Glu Val Asp Pro Asn Asp Arg Thr Lys Glu Ile
            115                 120                 125

Ser Glu Pro Phe Glu Ile Glu Gly Trp Thr Lys Phe Thr Phe Pro Gly
130                 135                 140

Arg Gly Asp Gln Tyr Ser Ser Phe Lys Trp Asn Ser Glu His Phe Asn
145                 150                 155                 160

Gly Thr Asp Phe Asp Ala Arg Glu Glu Arg Thr Gly Val Phe Arg Ile
                165                 170                 175

Ala Gly Glu Asn Lys Lys Trp Asn Glu Asn Val Asp Asp Glu Phe Gly
            180                 185                 190

Asn Tyr Asp Tyr Leu Met Phe Ala Asn Ile Asp Tyr Asn His Pro Asp
        195                 200                 205

Val Arg Arg Glu Met Ile Asp Trp Gly Lys Trp Leu Ile Asp Thr Leu
210                 215                 220

Gln Cys Gly Gly Phe Arg Leu Asp Ala Ile Lys His Ile Asn His Glu
225                 230                 235                 240

Phe Ile Lys Glu Phe Ala Ala Glu Met Ile Arg Lys Arg Gly Gln Asp
                245                 250                 255

Phe Tyr Ile Val Gly Glu Phe Trp Asn Ser Asn Leu Asp Ala Cys Arg
            260                 265                 270

Glu Phe Leu Asp Thr Val Asp Tyr Gln Ile Asp Leu Phe Asp Val Ser
        275                 280                 285

Leu His Tyr Lys Leu His Glu Ala Ser Leu Lys Gly Arg Asp Phe Asp
    290                 295                 300

Leu Ser Lys Ile Phe Asp Asp Thr Leu Val Gln Thr His Pro Thr His
305                 310                 315                 320

Ala Val Thr Phe Val Asp Asn His Asp Ser Gln Pro His Glu Ala Leu
                325                 330                 335

Glu Ser Trp Ile Gly Asp Trp Phe Lys Pro Ser Ala Tyr Ala Leu Thr
            340                 345                 350

Leu Leu Arg Arg Asp Gly Tyr Pro Val Val Phe Tyr Gly Asp Tyr Tyr
        355                 360                 365

Gly Ile Gly Gly Pro Glu Pro Val Asp Gly Lys Lys Glu Ile Leu Asp
    370                 375                 380

Ile Leu Leu Ser Ala Arg Cys Asn Lys Ala Tyr Gly Glu Gln Glu Asp
385                 390                 395                 400

Tyr Phe Asp His Ala Asn Thr Ile Gly Trp Val Arg Arg Gly Val Glu
                405                 410                 415

Glu Ile Glu Gly Ser Gly Cys Ala Val Val Ile Ser Asn Gly Asp Asp
            420                 425                 430

Gly Glu Lys Arg Met Phe Ile Gly Glu His Arg Ala Gly Glu Val Trp
        435                 440                 445

Val Asp Leu Thr Lys Ser Cys Asp Asp Gln Ile Thr Ile Glu Glu Asp
    450                 455                 460

Gly Trp Ala Thr Phe His Val Cys Gly Gly Val Ser Val Trp Ala
465                 470                 475                 480

Leu Pro Glu Gln Asn Glu Asp Cys Ala Asp Ala Glu
            485                 490

<210> SEQ ID NO 10
<211> LENGTH: 485
<212> TYPE: PRT
<213> ORGANISM: Bacillus sp.

<400> SEQUENCE: 10

```
His His Asn Gly Thr Asn Gly Thr Met Met Gln Tyr Phe Glu Trp His
1               5                   10                  15
Leu Pro Asn Asp Gly Asn His Trp Asn Arg Leu Arg Asp Asp Ala Ser
            20                  25                  30
Asn Leu Arg Asn Arg Gly Ile Thr Ala Ile Trp Ile Pro Pro Ala Trp
        35                  40                  45
Lys Gly Thr Ser Gln Asn Asp Val Gly Tyr Gly Ala Tyr Asp Leu Tyr
50                  55                  60
Asp Leu Gly Glu Phe Asn Gln Lys Gly Thr Val Arg Thr Lys Tyr Gly
65                  70                  75                  80
Thr Arg Ser Gln Leu Glu Ser Ala Ile His Ala Leu Lys Asn Asn Gly
                85                  90                  95
Val Gln Val Tyr Gly Asp Val Val Met Asn His Lys Gly Gly Ala Asp
            100                 105                 110
Ala Thr Glu Asn Val Leu Ala Val Glu Val Asn Pro Asn Asn Arg Asn
        115                 120                 125
Gln Glu Ile Ser Gly Asp Tyr Thr Ile Glu Ala Trp Thr Lys Phe Asp
130                 135                 140
Phe Pro Gly Arg Gly Asn Thr Tyr Ser Asp Phe Lys Trp Arg Trp Tyr
145                 150                 155                 160
His Phe Asp Gly Val Asp Trp Asp Gln Ser Arg Gln Phe Gln Asn Arg
                165                 170                 175
Ile Tyr Lys Phe Arg Gly Asp Gly Lys Ala Trp Asp Trp Glu Val Asp
            180                 185                 190
Ser Glu Asn Gly Asn Tyr Asp Tyr Leu Met Tyr Ala Asp Val Asp Met
        195                 200                 205
Asp His Pro Glu Val Val Asn Glu Leu Arg Arg Trp Gly Glu Trp Tyr
210                 215                 220
Thr Asn Thr Leu Asn Leu Asp Gly Phe Arg Ile Asp Ala Val Lys His
225                 230                 235                 240
Ile Lys Tyr Ser Phe Thr Arg Asp Trp Leu Thr His Val Arg Asn Ala
                245                 250                 255
Thr Gly Lys Glu Met Phe Ala Val Ala Glu Phe Trp Lys Asn Asp Leu
            260                 265                 270
Gly Ala Leu Glu Asn Tyr Leu Asn Lys Thr Asn Trp Asn His Ser Val
        275                 280                 285
Phe Asp Val Pro Leu His Tyr Asn Leu Tyr Asn Ala Ser Asn Ser Gly
290                 295                 300
Gly Asn Tyr Asp Met Ala Lys Leu Leu Asn Gly Thr Val Val Gln Lys
305                 310                 315                 320
His Pro Met His Ala Val Thr Phe Val Asp Asn His Asp Ser Gln Pro
                325                 330                 335
Gly Glu Ser Leu Glu Ser Phe Val Gln Glu Trp Phe Lys Pro Leu Ala
            340                 345                 350
Tyr Ala Leu Ile Leu Thr Arg Glu Gln Gly Tyr Pro Ser Val Phe Tyr
        355                 360                 365
Gly Asp Tyr Tyr Gly Ile Pro Thr His Ser Val Pro Ala Met Lys Ala
370                 375                 380
Lys Ile Asp Pro Ile Leu Glu Ala Arg Gln Asn Phe Ala Tyr Gly Thr
385                 390                 395                 400
Gln His Asp Tyr Phe Asp His His Asn Ile Ile Gly Trp Thr Arg Glu
                405                 410                 415
```

```
Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
        450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 11
<211> LENGTH: 480
<212> TYPE: PRT
<213> ORGANISM: Bacillus sp.

<400> SEQUENCE: 11

Asp Gly Leu Asn Gly Thr Met Met Gln Tyr Tyr Glu Trp His Leu Glu
1               5                   10                  15

Asn Asp Gly Gln His Trp Asn Arg Leu His Asp Ala Ala Ala Leu
                20                  25                  30

Ser Asp Ala Gly Ile Thr Ala Ile Trp Ile Pro Pro Ala Tyr Lys Gly
            35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300
```

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
            325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
            355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
            405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
            435                 440                 445

Leu Thr Gly Asn Asn Gly Ala Ser Val Thr Ile Asn Gly Asp Gly Trp
450                 455                 460

Gly Glu Phe Phe Thr Asn Gly Gly Ser Val Ser Val Tyr Val Asn Gln
465                 470                 475                 480

<210> SEQ ID NO 12
<211> LENGTH: 586
<212> TYPE: PRT
<213> ORGANISM: Bacillus

<400> SEQUENCE: 12

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
    290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys Thr Ser Thr Ser Gln Ile Thr Phe Thr Val Asn
                485                 490                 495

Asn Ala Thr Thr Val Trp Gly Gln Asn Val Tyr Val Val Gly Asn Ile
            500                 505                 510

Ser Gln Leu Gly Asn Trp Asp Pro Val Asn Ala Val Gln Met Thr Pro
        515                 520                 525

Ser Ser Tyr Pro Thr Trp Val Val Thr Val Pro Leu Pro Gln Ser Gln
    530                 535                 540

Asn Ile Gln Phe Lys Phe Ile Lys Lys Asp Gly Ser Gly Asn Val Ile
545                 550                 555                 560

Trp Glu Asn Ile Ser Asn Arg Thr Tyr Thr Val Pro Thr Ala Ala Ser
                565                 570                 575

Gly Ala Tyr Thr Ala Asn Trp Asn Val Pro
            580                 585

<210> SEQ ID NO 13
<211> LENGTH: 583
<212> TYPE: PRT
<213> ORGANISM: Bacillus

<400> SEQUENCE: 13

```
Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415
```

```
Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
            515                 520                 525

Pro Thr Trp Lys Ala Thr Ile Ala Leu Pro Gln Gly Lys Ala Ile Glu
            530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
            580

<210> SEQ ID NO 14
<211> LENGTH: 485
<212> TYPE: PRT
<213> ORGANISM: Bacillus

<400> SEQUENCE: 14

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
            115                 120                 125

Gln Glu Ile Ser Gly Glu Tyr Thr Ile Glu Ala Trp Thr Lys Phe Asp
            130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
            195                 200                 205
```

```
Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
            420                 425                 430

Gly Pro Gly Gly Asn Lys Trp Met Tyr Val Gly Lys His Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 15
<211> LENGTH: 485
<212> TYPE: PRT
<213> ORGANISM: Bacillus

<400> SEQUENCE: 15

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80
```

```
Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
            115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Gly Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Asn
                485
```

```
<210> SEQ ID NO 16
<211> LENGTH: 485
<212> TYPE: PRT
<213> ORGANISM: Cytophaga

<400> SEQUENCE: 16

Ala Ala Thr Asn Gly Thr Met Met Gln Tyr Phe Glu Trp Tyr Val Pro
  1               5                  10                  15

Asn Asp Gly Gln Gln Trp Asn Arg Leu Arg Thr Asp Ala Pro Tyr Leu
             20                  25                  30

Ser Ser Val Gly Ile Thr Ala Val Trp Thr Pro Pro Ala Tyr Lys Gly
         35                  40                  45

Thr Ser Gln Ala Asp Val Gly Tyr Gly Pro Tyr Asp Leu Tyr Asp Leu
     50                  55                  60

Gly Glu Phe Asn Gln Lys Gly Thr Val Arg Thr Lys Tyr Gly Thr Lys
 65                  70                  75                  80

Gly Glu Leu Lys Ser Ala Val Asn Thr Leu His Ser Asn Gly Ile Gln
                 85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380
```

```
Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
            405                 410                 415

Gly Asp Ser Thr Lys Ala Lys Ser Gly Leu Ala Thr Val Ile Thr Asp
        420                 425                 430

Gly Pro Gly Gly Ser Lys Arg Met Tyr Val Gly Thr Ser Asn Ala Gly
    435                 440                 445

Glu Ile Trp Tyr Asp Leu Thr Gly Asn Arg Thr Asp Lys Ile Thr Ile
        450                 455                 460

Gly Ser Asp Gly Tyr Ala Thr Phe Pro Val Asn Gly Gly Ser Val Ser
465                 470                 475                 480

Val Trp Val Gln Gln
                485

<210> SEQ ID NO 17
<211> LENGTH: 486
<212> TYPE: PRT
<213> ORGANISM: Bacillus stearothermophilus

<400> SEQUENCE: 17

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270
```

```
Leu His Asn Tyr Ile Thr Lys Thr Asn Gly Thr Met Ser Leu Phe Asp
    275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr
                485
```

STABILIZATION OF ALPHA-AMYLASES TOWARDS CALCIUM DEPLETION AND ACIDIC PH

CROSS-REFERENCE TO RELATED APPLICATIONS

This application is a division of U.S. application Ser. No. 14/525,877 filed Oct. 28, 2014, now U.S. Pat. No. 9,273,297, which is a division of U.S. application Ser. No. 13/518,962 filed Jun. 25, 2012, now U.S. Pat. No. 8,900,848, which is a 35 U.S.C. 371 national application of PCT/EP2011/050074 filed Jan. 4, 2011 which claims priority or the benefit under 35 U.S.C. 119 of European application nos. 10150063.5 and 10150062.7 filed Jan. 4, 2010 and Jan. 4, 2010 and U.S. provisional application Nos. 61/292,324, 61/292,327, 61/304,092, 61/333,930, 61/354,775, 61/354,817, 61/355, 230 and 61/362,536 filed Jan. 5, 2010, Jan. 5, 2010, Feb. 12, 2010, May 12, 2010, Jun. 15, 2010, Jun. 15, 2010 Jun. 16, 2010 and Jul. 8, 2010 the contents of which are fully incorporated herein by reference.

REFERENCE TO SEQUENCE LISTING

This application contains a Sequence Listing in computer readable form, which is incorporated herein by reference.

FIELD OF THE INVENTION

The present invention relates to variants of an alpha-amylase having improved stability at an acidic pH and/or in the presence of strong chelators compared to its parent enzyme. Further, the invention relates to nucleic acids encoding the variants, methods of producing the variants, and methods for using the variants.

BACKGROUND OF THE INVENTION

Alpha-amylases (alpha-1,4-glucan-4-glucanohydrolases, E.C. 3.2.1.1) constitute a group of enzymes, which catalyzes hydrolysis of starch and other linear and branched 1,4-gluosidic oligo- and polysaccharides.

There is a long history of industrial use of alpha-amylases in several known applications such as detergent, baking, brewing, starch liquefaction and saccharification, e.g., in preparation of high fructose syrups or as part of ethanol production from starch. These and other applications of alpha-amylases are known and utilize alpha-amylases derived from microorganisms, in particular bacterial alpha-amylases.

Among the first bacterial alpha-amylases to be used was an alpha-amylase from *B. licheniformis*, also known as Termamyl, which has been extensively characterized and the crystal structure has been determined for this enzyme. Alkaline amylases, such as AA560 (SEQ ID NO: 2), disclosed in WO 00/60060, form a particular group of alpha-amylases that have found use in detergents. Many of these known bacterial amylases have been modified in order to improve their functionality in a particular application.

Termamyl and many highly efficient alpha-amylases required calcium for activity. In the crystal structure for Termamyl it was found that four calcium atom were bound in the alpha-amylase structure coordinated by negatively charged amino acid residues. This requirement for calcium is a disadvangtage in applications where strong chelating compounds are present, such as in detergents or during ethanol production from whole grains, where plant material comprising high amount of natural chelaters such as phytate is hydrolysed using alpha-amylases.

Calcium-insensitive amylases are known, e.g., the alpha-amylases disclosed in EP 1022334 and WO 03/083054, and a *Bacillus circulans* alpha-amylase having the sequence disclosed in UNIPROT:Q03657, but these amylases are inferior to many of the calcium-sensitive amylase when it comes to starch hydrolysis and starch removal in various applications.

It would therefore be beneficial to provide variants of a calcium-sensitive alpha-amylase with reduced calcium sensitivity compared to its parent enzyme.

SUMMARY OF THE INVENTION

The present invention relates to isolated variants of a parent Termamyl-like alpha-amylase, comprising an alteration at two, three, four or five positions corresponding to positions 163, 188, 205, 208 and 209 of amino acids 1 to 485 of SEQ ID NO: 2 wherein the alteration(s) are independently (i) an insertion of an amino acid immediately downstream of the position, (ii) a deletion of the amino acid which occupies the position, and/or (iii) a substitution of the amino acid which occupies the position, and wherein the variants have alpha-amylase activity.

The variants of the invention may further comprise one or more additional substitution(s).

Additionally, the isolated variants may comprise further alterations known to improve the performance of alpha-amylases including a deletion corresponding to amino acids 183 and 184 and substitutions in one or more of the positions 186, 193, 195, 202, 206, 214, 244, 452, 474 and 475, and each position corresponds to a position of the amino acid sequence of the enzyme having the amino acid sequence of SEQ ID NO: 2.

The variants of the invention have reduced calcium sensitivity compared with the parent alpha-amylase.

The present invention also relates to isolated nucleotide sequences encoding the variant alpha-amylases or polypeptides having alpha-amylase activity and to nucleic acid constructs, vectors, and host cells comprising the nucleotide sequences.

Methods for preparing the variants of the invention are also provided.

The present invention also relates to compositions comprising the variants of the invention, in particular a detergent additive composition, detergent composition, composition for manual or automatic dishwashing or compositions for manual or automatic laundry washing. Further, the invention relates to the use of an alpha-amylase variant according to the invention for washing and/or dishwashing, textile desizing and starch liquefaction. The invention also relates to a method for producing ethanol or other chemicals using the variant of the invention.

DETAILED DESCRIPTION OF THE INVENTION

Definitions

Alpha-Amylases (alpha-1,4-glucan-4-glucanohydrolases, E.C. 3.2.1.1) constitute a group of enzymes, which catalyze hydrolysis of starch and other linear and branched 1,4-gluosidic oligo- and polysaccharides.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of the variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to additional nucleotides that provide for its expression.

Fragment: The term "fragment" means a polypeptide having one or more (several) amino acids deleted from the amino and/or carboxyl terminus of a mature polypeptide; wherein the fragment has alpha-amylase activity.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Improved pH stability: The term "improved pH stability" is defined herein as a variant enzyme displaying retention of enzymatic activity after a period of incubation at a particular pH, which reduces the enzymatic activity of the parent enzyme. Improved pH stability may also result in variants better able to catalyze a reaction under such pH conditions.

Isolated variant: The terms "isolated" and "purified" mean a polypeptide or polynucleotide that is removed from at least one component with which it is naturally associated. For example, a variant may be at least 1% pure, e.g., at least 5% pure, at least 10% pure, at least 20% pure, at least 40% pure, at least 60% pure, at least 80% pure, and at least 90% pure, as determined by SDS-PAGE and a polynucleotide may be at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Parent Enzyme: The term "parent" alpha-amylase as used herein means an alpha-amylase to which modifications, e.g., substitution(s), insertion(s), deletion(s), and/or truncation(s), are made to produce the enzyme variants of the present invention. This term also refers to the polypeptide with which a variant is compared and aligned. The parent may be a naturally occurring (wild type) polypeptide, or it may be a variant thereof, prepared by any suitable means. For instance, the parent protein may be a variant of a naturally occurring polypeptide which has been modified or altered in the amino acid sequence. A parent may also be an allelic variant which is a polypeptide encoded by any of two or more alternative forms of a gene occupying the same chromosomal locus.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (several) nucleotides deleted from the 5'- and/or 3'-end of a mature polypeptide coding sequence; wherein the subsequence encodes a fragment having alpha-amylase activity.

Variant: The term "variant" is defined herein as an alpha-amylase comprising one or more alterations, such as substitutions, insertions, deletions, and/or truncations of one or more specific amino acid residues at one or more specific positions in the polypeptide.

Wild-Type Enzyme: The term "wild-type" alpha-amylase denotes an alpha-amylase expressed by a naturally occurring microorganism, such as an yeast or filamentous fungus found in nature.

Conventions for Designation of Variants

In the present invention, a specific numbering of amino acid residue positions in the alpha-amylase variants is employed. For example, by aligning the amino acid sequences of known alpha-amylases, it is possible to designate an amino acid position number to any amino acid residue in any alpha-amylase enzyme.

Using the numbering system originating from the amino acid sequence of the alpha-amylase disclosed in SEQ ID NO: 2, aligned with the amino acid sequence of a number of other alpha-amylases, it is possible to indicate the position of an amino acid residue in an alpha-amylase in regions of structural homology.

In describing the various alpha-amylase variants of the present invention, the nomenclature described below is adapted for ease of reference. In all cases, the accepted IUPAC single letter or triple letter amino acid abbreviation is employed.

Substitutions.

For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively. In case that an amino acid substitution in a particular position is specified where the position can be occupied by different amino acids depending of the actual parent the original amino acid is indicated as X or Xaa. For example "X226A" is intended to mean that the amino acid that occupies position 226 is substituted with A or Ala, independently of which amino acid occupies position 226 in the original sequence (parent sequence).

Deletions.

For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*"

Insertions.

For an amino acid insertion, the following nomenclature is used: Original amino acid, position, original amino acid, new inserted amino acid. Accordingly the insertion of lysine after glycine at position 195 is designated "Gly195GlyLys" or "G195GK". Multiple insertions of amino acids are designated [Original amino acid, position, original amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent: | Variant: |
|---|---|
| 195 | 195 195a 195b |
| G | G - K - A |

Degenerate Indications.

For degenerate indications where an amino acid residue identical to the existing amino acid residue is inserted, degeneracy in the nomenclature arises. For example, a glycine inserted after the glycine in the above example would be indicated by "G195GG". Given that an alanine were present at position 194, the same actual change could just as well be indicated as "A194AG":

| | Parent: | Variant: |
|---|---|---|
| Numbering I: | 194 195 | 194 195 195a |
| Sequence: | A - G | A - G - G |
| Numbering II: | | 194 194a 195 |

Such instances will be apparent to the skilled person, and the indication "G195GG" and corresponding indications for this type of insertion is thus meant to comprise such equivalent degenerate indications.

If amino acid sequence segments are repeated in the parent polypeptide and/or in the variant, equivalent degenerate indications arise, also when alterations other than insertions are listed such as deletions and/or substitutions. For example, the deletion of two consecutive amino acids "AG" in the sequence "AGAG" from position 194-97 may be written as "A194*+G195*" or "A196*+G197*":

| | Parent: | Variant: |
|---|---|---|
| Numbering I: | 194 195 196 197 | 194 195 |
| Sequence: | A - G - A - G | A - G |
| Numbering II: | | 196 197 |

Multiple modifications. Variants comprising multiple modifications are separated by addition marks ("+"), e.g., "Arg170Tyr+Gly195Glu" or "R170Y+G195E" representing modifications at positions 170 and 195 substituting tyrosine and glutamic acid for arginine and glycine, respectively. Thus, "Tyr167Gly,Ala,Ser,Thr+Arg170Gly,Ala,Ser,Thr" designates the following variants:

"Tyr167Gly+Arg170Gly", "Tyr167Gly+Arg170Ala", "Tyr167Gly+Arg170Ser",
"Tyr167Gly+Arg170Thr", "Tyr167Ala+Arg170Gly", "Tyr167Ala+Arg170Ala",
"Tyr167Ala+Arg170Ser", "Tyr167Ala+Arg170Thr", "Tyr167Ser+Arg170Gly",
"Tyr167Ser+Arg170Ala", "Tyr167Ser+Arg170Ser", "Tyr167Ser+Arg170Thr",
"Tyr167Thr+Arg170Gly", "Tyr167Thr+Arg170Ala", "Tyr167Thr+Arg170Ser", and
"Tyr167Thr+Arg170Thr".

This nomenclature is particularly relevant to modifications involving substituting, inserting or deleting amino acid residues having specific common properties. Such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse (Taylor, 1986, *Journal of Theoretical Biology* 119: 205-218; compbio.dundee.ac.uk/papers/amas/amas3d.html).

Parent Alpha-Amylases

The parent alpha-amylase may in principle be any alpha-amylase for which it is desired to prepare a variant having improved stability at low pH. Alpha-amylases are known derived from a vide selection of organism including bacteria, such as from species of the genus *Bacillus*, e.g., *Bacillus licheniformis*; from species of fungi, such as *Aspergillus oryzae* (TAKA-amylase) or *Aspergillus niger*; from plants such as barley and from mammals. The parent alpha-amylse may in principle be any such alpha-amylase irrespective of the origin.

Termamyl-Like Alpha-Amylases

It is well known that a number of alpha-amylases produced by *Bacillus* spp. are highly homologous on the amino acid level as well as on the structural level. For instance, the *B. licheniformis* alpha-amylase comprising the amino acid sequence shown in SEQ ID NO: 4 (commercially available as Termamyl™) has been found to be about 81% homologous with the *B. amyloliquefaciens* alpha-amylase comprising the amino acid sequence shown in SEQ ID NO: 6 and about 60% homologous with the *B. stearothermophilus* alpha-amylase comprising the amino acid sequence shown in SEQ ID NO: 8. Further homologous alpha-amylases include an alpha-amylase derived from a strain of the *Bacillus* sp. NCIB 12289, NCIB 12512, NCIB 12513 or DSM 9375, all of which are described in detail in WO 95/26397, and the SP#707 alpha-amylase described by Tsukamoto et al., 1988, *Biochemical and Biophysical Research Communications* 151: 25-31.

Still further homologous alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: Optitherm™ and Takatherm™ (available from Solvay); Maxamyl™ (available from Gist-brocades/Genencor), Spezym AA™ and Spezyme Delta AA™, Spezyme FRED (available from Genencor), and Keistase™ (available from Daiwa), Purastar™ ST 5000E, PURASTRA™ HPAM L (from Genencor Int.).

Because of the substantial homology found between these alpha-amylases, they are considered to belong to the same class of alpha-amylases, namely the class of "Termamyl-like alpha-amylases".

Accordingly, in the present context, the term "Termamyl-like alpha-amylase" is intended to indicate an alpha-amylase, which at the amino acid level exhibits a substantial homology to Termamyl™, i.e., the *B. licheniformis* alpha-amylase having the amino acid sequence shown in SEQ ID NO: 4. In other words, a Termamyl-like alpha-amylase is an alpha-amylase, which has the amino acid sequence shown in SEQ ID NO: 2, 4, or 6, and the amino acid sequence shown in SEQ ID NO: 1 or 2 of WO 95/26397 or in Tsukamoto et al. (1988), or the *Bacillus flavothermus* amylase, AMY1048 described in WO 2005/001064, or the alpha-amylase TS-22 having the amino acid sequence of SEQ ID NO: 12; or the alpha-amylase TS-23 having the amino acid sequence of SEQ ID NO: 13, described in *J. Appl. Microbiology*, 1997, 82: 325-334 (SWALL: q59222), or the alpha-amylase derived from *Bacillus* sp. KSM-AP1378 (FERM BP-3048) having the amino acid sequence of SEQ ID NO: 14, described in WO 97/00324, or the alpha-amylase derived from *Bacillus* sp. A 7-7 having the amino acid sequence of SEQ ID NO: 15, described in WO 02/10356 or the *Cytophaga* alpha-amylase having the amino acid sequence of SEQ ID NO: 16, described in Jeang et al., 2002, *Appl. Environ. Microbiol.* 68:3651-3654, or the alpha-amylase derived from *Bacillus stearothermophilus* (Spezyme Xtra), having the amino acid sequence of SEQ ID NO: 17; or the alpha-amylase produced by the *B. licheniformis* strain described in EP 0252666 (ATCC 27811) or the alpha-amylases disclosed in WO 91/00353 and WO 94/18314 or i) which displays at least 60%, preferred at least 70%, more preferred at least 75%, even more preferred at least 80%, especially at least 85%, especially preferred at least 90%, even especially more preferred at least 95% homology, more preferred at least 97%, more preferred at least 99% with at least one of said amino acid sequences and/or ii) displays immunological cross-reactivity with an antibody raised against at least one of said alpha-amylases, and/or iii) is encoded by a DNA sequence which hybridises to the DNA sequences encoding the above-specified alpha-amylases which are apparent from SEQ ID NOS: 1, 3, and 5 of the present application and SEQ ID NOS: 4 and 5 of WO 95/26397, respectively.

In a preferred embodiment the parent Termamyl-like alpha amylase is SEQ ID NO: 10 (SEQ ID NO: 2 of WO 95/26397), SEQ ID NO: 8 or SEQ ID NO: 2 including any of [SEQ ID NO: 10]+R181*+G182*, [SEQ ID NO: 10]+D183*+G184*; [SEQ ID NO: 10]+D183*+G184*+N195F; [SEQ ID NO: 10]+D183*+G184*+M202L; [SEQ ID NO: 10]+D183*+G184*+N195F+M202L; [SEQ ID NO: 10]+D183*+G184*+R181Q; [SEQ ID NO: 10]+D183*+G184*+R118K+N195F+R320K+R458K; [SEQ ID NO: 8]+I181*+G182*; [SEQ ID NO: 8]+I181*+G182*+N193F; [SEQ ID NO: 8]+I181*+G182*+M200L; [SEQ ID NO: 8]+I181*+G182*+N193F+M200L; [SEQ ID NO: 10]+D183*+G184*; [SEQ ID NO: 10]+D183*+G184*+N195F; [SEQ ID NO: 10]+D183*+G184*+M202L; [SEQ ID NO: 10]+D183*+G184*+N195F+M202L; [SEQ ID NO: 10]+D183*+G184*+R118K+N195F+R320K+R458K. [SEQ ID NO: 8]+I181*+G182*+N193F" means the *B. stearothermophilus* alpha-amylasehaving SEQ ID NO: 8 has been mutated as follows: deletions in positions 1181 and G182 and a substitution from Asn (N) to Phe (F) in position 193.

Parent Hybrid Alpha-Amylases

The parent alpha-amylase may be a hybrid alpha-amylase, i.e., an alpha-amylase, which comprises a combination of partial amino acid sequences derived from at least two alpha-amylases.

The parent hybrid alpha-amylase may be one, which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase, from which a partial amino acid sequence derives, may, e.g., be any of those specific Termamyl-like alpha-amylases referred to herein.

For instance, the parent alpha-amylase may comprise a C-terminal part of an alpha-amylase derived from a strain of *B. licheniformis*, and a N-terminal part of an alpha-amylase derived from a strain of *B. amyloliquefaciens* or from a strain of *B. stearothermophilus*. For instance, the parent alpha-amylase may comprise at least 430 amino acid residues of the C-terminal part of the *B. licheniformis* alpha-amylase, and may, e.g., comprise a) an amino acid segment corresponding to the 37 N-terminal amino acid residues of the *B. amyloliquefaciens* alpha-amylase having the amino acid sequence shown in SEQ ID NO: 6 and an amino acid segment corresponding to the 445 C-terminal amino acid residues of the *B. licheniformis* alpha-amylase having the amino acid sequence shown in SEQ ID NO: 4, or b) an amino acid segment corresponding to the 68 N-terminal amino acid residues of the *B. stearothermophilus* alpha-amylase having the amino acid sequence shown in SEQ ID NO: 8 and an amino acid segment corresponding to the 415 C-terminal amino acid residues of the *B. licheniformis* alpha-amylase having the amino acid sequence shown in SEQ ID NO: 4.

In a preferred embodiment the parent Termamyl-like alpha-amylase is a hybrid Termamyl-like alpha-amylase identical to the *Bacillus licheniformis* alpha-amylase shown in SEQ ID NO: 4, except that the N-terminal 35 amino acid residues (of the mature protein) is replaced with the N-terminal 33 amino acid residues of the mature protein of the *Bacillus amyloliquefaciens* alpha-amylase (BAN) shown in SEQ ID NO: 6. Said hybrid may further have the following mutations: H156Y+A181T+N190F+A209V+Q264S (using the numbering in SEQ ID NO: 4) referred to as LE174.

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures, which are markedly different from the structure of a typical Termamyl-like alpha-amylase as referred to herein.

The fungal alpha-amylases mentioned above, i.e., derived from *A. niger* and *A. oryzae*, are highly homologous on the amino acid level and generally considered to belong to the same family of alpha-amylases. The fungal alpha-amylase derived from *Aspergillus oryzae* is commercially available under the tradename Fungamyl™

Furthermore, when a particular variant of a Termamyl-like alpha-amylase (variant of the invention) is referred to—in a conventional manner—by reference to modification (e.g., deletion or substitution) of specific amino acid residues in the amino acid sequence of a specific Termamyl-like alpha-amylase, it is to be understood that variants of another Termamyl-like alpha-amylase modified in the equivalent position(s) (as determined from the best possible amino acid sequence alignment between the respective amino acid sequences) are encompassed thereby.

A preferred variant of the invention is one derived from a *B. licheniformis* alpha-amylase (as parent Termamyl-like alpha-amylase), e.g., one of those referred to above, such as the *B. licheniformis* alpha-amylase having the amino acid sequence shown in SEQ ID NO: 4.

Variants

The present invention relates to isolated variant alpha-amylases of a parent Termamyl-like alpha-amylase comprising two, three, four or five amino acid alterations in positions corresponding to positions in the parent alpha-amylase selected from the group consisting of 163, 188, 205, 208 and 209; the alteration(s) are independently (i) an insertion of an amino acid immediately downstream of the position, (ii) a deletion of the amino acid which occupies the position, and/or (iii) a substitution of the amino acid which occupies the position, wherein the variant has alpha-amylase activity and have reduced calcium sensitivity compared with the parent alpha-amylase, and wherein each position corresponds to a position of the amino acid sequence of the enzyme having the amino acid sequence of SEQ ID NO: 2.

The variant may be a natural or a non-natural variant, where natural variants should be understood as an alpha-amylase isolated from a naturally occurring organism that have not been the subject of human manipulation. A non-natural variant is a variant that have been modified from its natural counterpart, the parent alpha-amylase, by human intervention using techniques such as mutation of a wild type organism and isolation of variant alpha-amylases, techniques involving isolation and manipulation of nucleic acids encoding a parent alpha-amylase or chemical synthesis of the variants of nucleic acids encoding them. Many such techniques are available in the art and the skilled person will appreciate that such techniques can be applied in the present invention.

The variants of the invention are generally isolated using at least one separation step, and the invention does therefore not apply to natural enzymes in their natural environment.

The variants according to the invention have the benefit of being less sensitive toward calcium depletion than their parent alpha-amylase, but at the same time they have maintained the performance properties of the parent alpha-amylase. Calcium sensitivity is manifested in the activity and/or stability of the particular alpha-amylase in calcium-depleted environments and/or under acidic conditions. Calcium-depleted environments occur in many known applications for alpha-amylases, such as in the presence of strong chelators binding metal ions, in particular calcium ions, e.g., in detergents, where it is common to include strong chelators because of the beneficial effect of the laundering process, or in conditions where plant material including natural chelators such as phytates or citrates is present. Such strong chelators will compete for the calcium ions and will to some extend be able to deprive calcium-sensitive alpha-amylases for the calcium ions bound in their structure with the consequence that the stability or activity of the calcium sensitive alpha-amylase is reduced.

Acidic conditions may also affect the stability or activity of calcium-sensitive alpha-amylases. It is believed that low pH may lead to a protonation of the amino acid residues that coordinates the calcium ions in sensitive alpha-amylases with the result that they no longer is capable of binding the calcium and the result is a loss of stability and/or activity. As examples of applications where alpha-amylases are exposed to acidic conditions can be mentioned use of alpha-amylases as in treatment of digestive disorders such as disclosed in WO 2006/136161, and use in feed.

Thus, the variants of the invention have at least one of the properties: improved stability and/or activity in the presence of strong chelators and/or improved stability and/or activity at low pH, and it should be understood in this specification and claims that a variant having reduced calcium sensitivity has improved stability and/or activity in the presence of strong chelators and/or improved stability and/or activity at low pH.

Chelator strength may be evaluated using methods known in the art such as methods disclosed in *Anal. Biochem.* 314: 227-234 (2003), and *JAOCS* 61(9): 1475-1478 (1984). As examples of strong chelators that may be used for such an assay can be mentioned EGTA (ethylene glycol tetraacetic acid), EDTA (ethylene diamine tetraacetic acid), DTPA (diethylene triamine pentaacetic acid), DTMPA (diethylene triamine-penta-methylene phosphonic acid) and HEDP (1-hydroxyethan-1,1-diylbis(phosphonic acid)). The skilled person will be able to select other strong chelators that may be used in determining the calcium sensitivity of an alpha-amylase.

In the present invention, the isolated variants of a parent termamyl-like alpha-amylase comprise an alteration at two, three, four or five positions, said positions corresponding to positions in the parent alpha-amylase selected from the group consisting of: 163, 188, 205, 208 and 209 wherein the alteration(s) are independently (i) an insertion of an amino acid immediately downstream of the position, (ii) a deletion of the amino acid which occupies the position, and/or (iii) a substitution of the amino acid which occupies the position, wherein the variant has alpha-amylase activity; and each position corresponds to a position of the amino acid sequence of the enzyme having the amino acid sequence of SEQ ID NO: 2.

Preferably the variants comprises alterations at three positions, more preferred four positions even more preferred five positions and most preferred six positions, said positions corresponding to positions in the parent alpha-amylase selected from the group consisting of: 163, 188, 205, 208 and 209 using SEQ ID NO: 2 for numbering.

The alterations may be selected among:

X163A,C,E,F,G,H,I,K,L,M,N,P,Q,R,S,T,V,W,Y, preferably X163Q or X163N;

X188A,C,E,F,G,H,I,K,L,M,N,P,Q,R,S,T,V,W,Y, preferably X188N;

X205A,C,E,F,G,H,I,K,L,M,N,P,Q,R,S,T,V,W,Y, preferably X205N;

X208A,C,D,E,F,G,H,I,K,L,N,P,Q,R,S,T,V,W,Y, preferably X208F or X208Y; and

X209A,C,E,F,G,H,I,K,L,M,N,P,Q,R,S,T,V,W,Y, preferably X209S or X209N.

Preferred variants comprise the mutations D163Q+D188N+D209N,S or the mutations D163Q, N+D188N+M208F+D209S+K242P+S244W.

The variants may further comprise additional alteration(s) in one or more amino acid residues of the parent alpha-amylase.

Preferred further alterations include alterations where one or more amino acids in the B-domain of the parent alpha-amylase are substituted with the corresponding amino acids of *B. circulans* alpha-amylase having SEQ ID NO: 9 or *Bacillus* sp. KSM-K38 alpha-amylase SEQ ID NO: 11. In case that a particular amino acid residue in the B-domain of a parent alpha-amylase is missing in SEQ ID NO: 9 or SEQ ID NO: 11the preferred alteration is a deletion of the particular amino acid. The skilled person will appreciate that such a substitution of an amino acid residue in the B-domain of the parent alpha-amylase with the corresponding amino acid in SEQ ID NO: 9 or SEQ ID NO: 11 is only relevant for positions where the two amino acid sequences differ. Consequently, the number of possible alterations in this group will vary depending on the particular parent alpha-amylase and the sequence identity between the parent alpha-amylase and the alpha-amylase having the sequence shown in SEQ ID NO: 9 or SEQ ID NO: 11.

The inventors have found that such further alterations provides for variants having an even more reduced calcium sensitivity compared with the parent alpha-amylase.

The B-domain of alpha-amylases is well known in the art and methods for identifying B-domains known in the art can also be applied to the present invention. The B-domain of alpha-amylases can be determined by structure analysis such as by using crystallographically techniques for identification of the domain structure of a given alpha-amylase. For example, Machius et al., 1995, *J. Mol. Biol.* 4: 545-559 and Machius et al., 1998, *Structure* 6:281-292, identified the B-domain in *B. licheniformis* alpha-amylase as residues 104-204; Brzozowski et al., 2000, *Biochemistry* 39:9099-9017 identified the B-domain in a hybrid alpha-amylase consisting of amino acids 1-300 of *B. amyloliquefaciens* alpha-amylase and amino acid residues 301-483 of *B. licheniformis* alpha-amylase as residues 104-205; Suvd et al., 2001, *J. Biochem.* 129:461-468, identified the B-domain in *B. stearothermophilus* alpha amylase and Nonaka et al. (2008) identified the B-domain of the alpha-amylase from *Bacillus* sp. KSM-K38.

An alternative method for determining the B-domain for a given alpha-amylase is by sequence alignment of the amino acid sequence of the given alpha-amylase and an alpha-amylase for which the B-domain has been determined. The two sequences are aligned and the sequence in the given alpha-amylase sequence that aligns with the B-domain sequence in the alpha-amylase for which the B-domain has been determined can for the purpose of this invention be considered the B-domain for the given alpha-amylase. This method is particular suitable for alpha-amylases for which the three-dimensional structure is not available. However, for alpha-amylases where the B-domain has been determined based on the three-dimensional structure of the alpha-amylase, the B-domain determined by the latter method should preferentially be used in case that the B-domain determined by alignment differs from the B-domain determined based on the structure.

The variants of the invention may even comprise further alterations known in the art to improve the performance of alpha-amylases. For example may oxidizable amino acid residues be substituted with a non-oxidizable amino acid residue in order to improve the stability of the enzyme under oxidizing conditions, e.g., in the presence of bleach, in accordance with the teachings of WO 94/18314 and WO 94/02597, incorporated herein by reference.

A two amino acid deletion may be introduced in positions corresponding to R181+G182 or T183+G184 in SEQ ID NO: 2 in accordance with the teachings of WO 96/23873, incorporated by reference.

Further beneficial substitutions that may be introduced into the variants of the invention can be found in WO 99/23211, WO 01/66712, WO 02/10355 and WO 2006/002643 all included by reference.

As examples of preferred further alterations can be mentioned D183*+G184*, G186A,Y,T, T193F, N195F, M202L, I,T,S,A, I206F,Y, V214I, S244A,D,E,N,Q,W, T452H,Y, G474R, G475R, wherein each position corresponds to a position of the amino acid sequence of the enzyme having the amino acid sequence of SEQ ID NO: 2. The skilled person will appreciate that corresponding alteration can be identified and performed starting from other parent alpha-amylases.

The number of amino acid substitutions in the variants of the present invention comprise preferably less than 60 substitutions, more preferred less than 55 substitutions, more preferred less than 50 substitutions, more preferred less than 45 substitutions, more preferred less than 40 substitutions, more preferred less than 35 substitutions, more preferred less than 30 substitutions, more preferred less than 25 substitutions, more preferred less than 20 substitutions, more preferred less than 15 substitutions, most preferred less than 10 substitutions.

The variants of the invention are preferably at least 70% identical to their parent alpha-amylase, more preferred at least 75% identical to their parent alpha-amylase; more preferred at least 80% identical to their parent alpha-amylase, more preferred at least 85% identical to their parent alpha-amylase more preferred at least 90% identical to their parent alpha-amylase more preferred at least 95% identical to their parent alpha-amylase, and most preferred at least 98% identical to their parent alpha-amylase.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 2.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 4.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 6.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 8.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 10.

In another embodiment, the variant has at least 70%, e.g., at least 75%, at least 80%, at least 85%, at least 90%, at least 91%, at least 92%, at least 93%, at least 94%, at least 95%, such as at least 96%, at least 97%, at least 98%, and at least 99%, but less than 100%, sequence identity to the mature polypeptide of SEQ ID NO: 11.

In on preferred embodiment the parent alpha-amylase is the alpha-amylase having the sequence disclosed in SEQ ID NO: 2. In this embodiment preferred substitutions according to the invention are selected among: D163Q,N, D188N, D205N, M208Y and D209N.

Alterations in the B-domain of SEQ ID NO: 2 include the alterations: A113E, M116V, V117F, R118K, A119V, V120I, N123D, N126D, N128T, Q129K, G133E, D134P, Y135F, T136E, A139G, D144T, N150D, T151Q, H152Y, N154S, R158N, W159S, Y160E, V165T, W167F, Q169A, S170R/K, R171E/G, K172E, L173R, N174*, N175T, R176G, I177V, Y178F, K179R, F180I, R181A, D183E, G184N, A186K, W189E, E190N, T193D, N195F, Y203F, E212D, V214R, and N215R.

As examples of further alterations known to increase performance of alpha-amylases can be mentioned: D183*+ G184*, G186A,Y or T, T193F, N195F, M202X preferably L,I,T,S or A, I206F or Y, V214I, S244A,D,E,N,Q or W, T452H or Y, G474R and G475R.

Preferred variants according to this embodiment include:
D163Q+D188N+M208F+D209S+K242P+S244W;
D163N+R181A+G182A+K185T+G186N+D188N+ D205N+M208F+D209S+V238I+K242P+S244W;
N128W+D163N+R181A+G182N+K185T+G186N+ D188N+D205N+M208F+D209S+K242P+S244W;
D163N+R181A+G183N+K185T+G186N+D188N+ D205N+M208F+D209S+K242P+S244W+H408W+ N409D+D432N+A434P;
D163N+R181A+G182N+K185T+G186N+D188N+ D205N+M208F+D209S+K242P+S244W+N409D+ D432N+A434P;
D163N+R181A+G182N+K185T+G186N+D188N+ D205N+M208F+D209S+K242P+S244W D183*+G184*+ R118K+N195F+R320K+R458K+D163Q+D188N+ M208F+D209S+K242P+S244W;
D183*+G184*+R118K+N195F+R320K+R458K+D163N+ R181A+G182A+K185T+G186N+D188N+D205N+ M208F+D209S+V238I+K242P+S244W;
D183*+G184*+R118K+N195F+R320K+R458K+N128W+ D163N+R181A+G182N+K185T+G186N+D188N+ D205N+M208F+D209S+K242P+S244W;
D183*+G184*+R118K+N195F+R320K+R458K+D163N+ R181A+G183N+K185T+G186N+D188N+D205N+ M208F+D209S+K242P+S244W+H408W+N409D+ D432N+A434P;
D183*+G184*+R118K+N195F+R320K+R458K;
D163N+R181A+G182N+K185T+G186N+D188N+ D205N+M208F+D209S+K242P+S244W;
D183*+G184*+R118K+N195F+R320K+R458K+D163N+ R181A+G182A+K185T+G186N+D188N+D205N+ M208F+D209S+V238I+K242P+S244W;
D188N+D209S; D163N+D188N+D209S;
D163N+D188N+D205N+D209S;
D163N+D188N+D205N+M208F+D209S;
D207N+D209S; D163N+D207N+D209S;
D163N+D188N+D207N+D209S;
D163N+D188N+D199N+D207N+D209S;
D163N+D188N+D199N+D205N+D207N+D209S;
D163N+D188N+D199N+D205N+M208F+D207N+ D209S;
D163N+R181A+G182N+G186N+D188N+D205N+D209S;
D163N+R181A+G182N+K185T+G186N+D188N+ D205N+D209S;
D163N+R181A+G182N+K185T+G186N+D188N+ D205N+M208F+D209S;
D163N+R181A+G182N+D188N+D199N+D205N+ M208F+D207N+D209S;
D163N+R181A+G182N+K185T+D188N+D199N+ D205N+M208F+D207N+D209S; and
D163N+R181A+G182N+K185T+G186N+D188N+ D199N+D205N+M208F+D207N+D209S.

In another preferred embodiment the parent alpha-amylase is SP722 having the sequence disclosed in SEQ ID NO: 10. In this embodiment preferred substitutions according to the invention are selected among: D163Q,N, D188N, D205N, M208Y and D209N.

Alterations in the B-domain of SEQ ID NO: 10 include the alterations: A113E, N116V, V117F, L118K, A119V, V120I, N123D, N126D, N128T, Q129K, G133E, D134P, Y135F, T136E, A139G, D144T, N150D, T151Q, D154S, R158N, W159S, Y160E, V165T, W167F, Q169A, S170R or K, R171E or G, Q172E, F173R, Q174*, N175T, R176G, I177V, Y178F, K179R, F180I, R181A, D183E, G184N, A186K, W189E, E190N, S193D, N195F, Y203F, V206I, E212D, V214R, and N215R.

As examples of further alterations known to increase performance of alpha-amylases can be mentioned: D183*+G184*, A186Y or T, S193F, N195F, M202X, preferably L,I,T,S or A, I206L or F, V214I, S244A,E or Q, H452Y, G474R and G475R.

As examples or preferred variants according to this embodiment can be mentioned:
D188N+D209S;
D163N+D188N+D209S;
D163N+D188N+D205N+D209S;
D163N+D188N+D205N+M208F+D209S;
D207N+D209S;
D163N+D207N+D209S;
D163N+D188N+D207N+D209S;
D163N+D188N+D199N+D207N+D209S;
D163N+D188N+D199N+D205N+D207N+D209S;
D163N+D188N+D199N+D205N+M208F+D207N+D209S;
D163N+R181A+G182N+G186N+D188N+D205N+D209S;
D163N+R181A+G182N+K185T+A186N+D188N+D205N+D209S;
D163N+R181A+G182N+K185T+A186N+D188N+D205N+M208F+D209S;
D163N+R181A+G182N+D188N+D199N+D205N+M208F+D207N+D209S;
D163N+R181A+G182N+K185T+D188N+D199N+D205N+M208F+D207N+D209S; and
D163N+R181A+G182N+K185T+A186N+D188N+D199N+D205N+M208F+D207N+D209S.

In a further preferred embodiment the parent alpha-amylase is the *B. stearothermophilus* alpha-amylase having the sequence disclosed in SEQ ID NO: 8. In this embodiment preferred substitutions are selected among: D162Q,N, D186N, D203N, M206Y and D207N.

Alterations in the B-domain of SEQ ID NO: 8 where an amino acid is substituted with the corresponding amino acid from the alpha-amylase having the sequence SEQ ID NO: 9 or deletions in case that no corresponding amino acid exists include the alterations: D105N, G108A, G112E, W115V, V116F, D117K, A118V, V119I, N122D, S124N, N127T, Q128K, G132E, T133P, Y134F, Q135E, A138G, D143T, N149D, T150Q, R157N, W158S, Y159E, V164T, W166F, E168A, S169K, R170G, K171E, L172R, S173T, R174G, I175V, Y176F, K177R, F178I, R179A, I181E, G182N, A184K, W187E, E188N, T191 D,Y201F, L204I and, E210D.

As examples of further alterations known to increase performance of alpha-amylases are: I181*+G182*, A184Y/T, N191F, N193F, M200X preferably L,I,T,S or A, L204F, M206Y, V212I, S242A,D,E,N or Q, H296Y, G474R and G475R.

As examples or preferred variants according to this embodiment can be mentioned:
D207N+D186N;
D207N+D186N+D162N;
D207N+D186N+D162N+D203N;
D207N+D186N+D162N+D203N+M206Y;
D207N+D186N+D162N+D203N+M206Y+D105N;
D207N+A184K+W187E;
D162N+A184K+D186N+D207N;
D207N+A184K+W187E+D186N;
D207N+A184K+W187E+D186N+D162N;
D207N+A184K+W187E+D186N+D162N+D203N;
D207N+A184K+W187E+D186N+D162N+D203N+M206Y; and
D207N+A184K+W187E+D186N+D162N+D203N+M206Y+D105N.

Other preferred parent alpha-amylases includes: SEQ ID NO: 2 in WO 2005/001064, *B. licheniformis* alpha-amylase having the sequence SEQ ID NO: 4, *B. amyloliquefaciens* alpha-amylase having the sequence SEQ ID NO: 6, alpha-amylase derived from a strain of the *Bacillus* sp. NCIB 12289, NCIB 12512, NCIB 12513 or DSM 9375, all of which are described in detail in WO 95/26397, and the #707 alpha-amylase described by Tsukamoto et al., 1988, *Biochemical and Biophysical Research Communications*, 151: 25-31 and the alpha-amylase derived from KSM-Ap1378 and described in WO 94/26881.

Nucleotide Sequences

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labelled oligonucleotide probes may be synthesized and used to identify alpha-amylase-encoding clones from a genomic library prepared from the organism in question. Alternatively, a labelled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S. L. Beaucage and M. H. Caruthers (1981) or the method described by Matthes et al. (1984). In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al. (1988).

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Homology (Identity)

The homology may be determined as the degree of identity between the two sequences indicating a derivation of the first sequence from the second. The homology may suitably be determined by means of computer programs known in the art such as GAP provided in the GCG program package (described above). Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, 1970, *J. Mol. Biol.* 48: 443-453, to make alignments and to calculate the identity.

A structural alignment between Termamyl and a Termamyl-like alpha-amylase may be used to identify equivalent/corresponding positions in other Termamyl-like alpha-amylases. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., 1987, *FEBS Letters* 224: 149-155) and reverse threading (Huber et al., 1998, *Protein Science* 7(1): 142-149). Property ii) of the alpha-amylase, i.e., the immunological cross reactivity, may be assayed using an antibody raised against, or reactive with, at least one epitope of the relevant Termamyl-like alpha-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immunodiffusion assay, e.g., as described by Hudson et al., 1989. In this respect, immunological cross-reactivity between the alpha-amylases having the amino acid sequences SEQ ID NOS: 2, 4, 6, or 8, respectively, have been found.

Hybridization

The oligonucleotide probe used in the characterization of the Termamyl-like alpha-amylase may suitably be prepared on the basis of the full or partial nucleotide or amino acid sequence of the alpha-amylase in question.

Suitable conditions for testing hybridization involve presoaking in 5×SSC and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at ~40° C., followed by three times washing of the filter in 2×SSC, 0.2% SDS at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e., a variant, which is the result of a modification (insertion, substitution, deletion) of one or more amino acid residues of the naturally occurring alpha-amylase.

Production of Variant Alpha-Amylases

The variant alpha-amylases of the invention may be produced using methods well known in the area. Generally, DNA sequences encoding the parent alpha-amylase is provided and the desired alteration is generated in the nucleic acid sequence using techniques known in the art.

The generated DNA sequence encoding the desired variant alpha-amylase of the invention is provided with suitable regulatory sequences, such as promoter, terminator, activation sites, ribosome binding sites, polyadenylation sites etc. and introduced into a suitable host cell. Finally the host cell comprising said DNA is grown under conditions leading to expression of the variant alpha-amylase according to the invention.

All these techniques are known in the art and it is within the skills of the average practitioner within the field to prescribe a suitable method for producing a given variant alpha-amylase of the invention using techniques disclosed in well known text books such as Sambrook et al., Molecular Cloning: A Laboratory Manual, 2nd Ed., Cold Spring Harbor, 1989.

Further teachings regarding preparation of variant alpha-amylases can be found in WO 2006/002643, which is incorporated by reference, and the skilled person will appreciate that this teaching also applies to the present invention.

Compositions

The present invention also relates to compositions comprising an alpha-amylase variant and at least one additional enzyme. The additional enzyme(s) may be selected from the group consisting of beta-amylase, cellulase (beta-glucosidase, cellobiohydrolase and endoglucanase), glucoamylase, hemicellulsae (e.g., xylanase), isoamylase, isomerase, lipase, phytase, protease, pullulanase, and/or other enzymes useful in a commercial process in conjunction with an alpha-amylase. The additional enzyme may also be a second alpha-amylase. Such enzymes are known in the art in starch processing, sugar conversion, fermentations for alcohol and other useful end-products, commercial detergents and cleaning aids, stain removal, fabric treatment or desizing, and the like.

Methods of Using the Alpha-Amylase Variants—Industrial Applications

The variants of the present invention possess valuable properties allowing for a variety of industrial applications. In particular, the variants may be used in detergents, in particular laundry detergent compositions and dishwashing detergent compositions, hard surface cleaning compositions, and for desizing textiles, fabrics or garments, production of pulp and paper, beer making, ethanol production, and starch conversion processes.

The alpha-amylase variants may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the variant of the invention also comprise an AMG, pullulanase, and other alpha-amylases.

Further, the variants are particularly useful in the production of sweeteners and ethanol (see, e.g., U.S. Pat. No. 5,231, 017, which is hereby incorporated by reference), such as fuel, drinking and industrial ethanol, from starch or whole grains.

The variants may also be used for desizing of textiles, fabrics, and garments (see, e.g., WO 95/21247, U.S. Pat. No. 4,643,736, and EP 119920, which are incorporated herein by reference), beer making or brewing, and in pulp and paper production or related processes.

Starch Processing

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be suitably processed. This reduction in viscosity is primarily attained by enzymatic degradation in current commercial practice.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, preferably pH 7.5, and the calcium is removed by ion exchange. The dextrose syrup is then converted into high fructose syrup using, e.g., an immobilized glucose isomerase.

Production of Fermentation Products

In general, alcohol production (ethanol) from whole grain can be separated into 4 main steps: milling, liquefaction, saccharification, and fermentation.

The grain is milled in order to open up the structure and allow for further processing. Two processes used are wet or dry milling. In dry milling, the whole kernel is milled and used in the remaining part of the process. Wet milling gives a very good separation of germ and meal (starch granules and protein) and is with a few exceptions applied at locations where there is a parallel production of syrups.

In the liquefaction process the starch granules are solubilized by hydrolysis to maltodextrins mostly of a DP higher than 4. The hydrolysis may be carried out by acid treatment or enzymatically by an alpha-amylase. Acid hydrolysis is used on a limited basis. The raw material can be milled whole grain or a side stream from starch processing.

During a typical enzymatic liquefaction, the long-chained starch is degraded into branched and linear shorter units (maltodextrins) by an alpha-amylase. Enzymatic liquefaction is generally carried out as a three-step hot slurry process. The slurry is heated to between 60-95° C. (e.g., 77-86° C., 80-85° C., or 83-85° C.) and the enzyme(s) is (are) added. The liquefaction process is carried out at 85° C. for 1-2 hours. The pH is generally between 5.5 and 6.2. In order to ensure optimal enzyme stability under these conditions, 1 mM of calcium is added (to provide about 40 ppm free calcium ions). After such treatment, the liquefied starch will have a "dextrose equivalent" (DE) of 10-15.

The slurry is subsequently jet-cooked at between 95-140° C., e.g., 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

Liquefied starch-containing material is saccharified in the presence of saccharifying enzymes such as glucoamylases. The saccharification process may last for 12 hours to 120 hours (e.g., 12 to 90 hours, 12 to 60 hours and 12 to 48 hours).

However, it is common to perform a pre-saccharification step for about 30 minutes to 2 hours (e.g., 30 to 90 minutes) at a temperature of 30 to 65° C., typically around 60° C., which is followed by a complete saccharification during fermentation referred to as simultaneous saccharification and fermentation (SSF). The pH is usually between 4.2-4.8, e.g., 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of a glucoamylase and debranching enzyme. The saccharification process proceeds for 24-72 hours.

Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn. Accordingly, in the first aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. In an embodiment a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55, e.g., 25-45 and 30-40, w/w % dry solids (DS) of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %. Such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase variant, or;

(b) saccharifying the liquefied material obtained in step (a) using a carbohydrate-source generating enzyme;

(c) fermenting using a fermenting organism.

In an aspect, a pullulanase such as a family GH57 pullulanase is also used in the liquefaction step. In an embodiment a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In an embodiment the carbohydrate-source generating enzyme is a glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of the genus *Pachykytospora*, e.g., a strain of *Pachykytospora papyracea*; or a strain of the genus *Leucopaxillus*, e.g., *Leucopaxillus giganteus*; or a strain of the genus *Peniophora*, e.g., a strain of the species *Peniophora rufomarginata*; or a mixture thereof. Saccharification step (b) and fermentation step (c) may be carried out either sequentially or simultaneously. A pullulanase and/or metalloprotease may be added during saccharification and/or fermentation when the process is carried out as a sequential saccharification and fermentation process and before or during fermentation when steps (b) and (c) are carried out simultaneously (SSF process). The pullulanase and/or metalloprotease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment the particle size is smaller than a #7 screen, e.g., a #6 screen. A #7 screen is usually used in conventional prior art processes. The aqueous slurry may contain from 10-55 w/w % dry solids (DS), e.g., 25-45 and 30-40 w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Beer Making

The alpha-amylase variants may also be used in a beer-making process and similar fermentations; the alpha-amylases will typically be added during the mashing process. The process is substantially similar to the milling, liquefaction, saccharification, and fermentation processes described above.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to a phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

Currently, it is believed that commercially-available microbial alpha-amylases used in the liquefaction process are generally not stable enough to produce liquefied starch substrate from a dry mill process using whole ground grain at a temperature above about 80° C. at a pH level that is less than pH 5.6. The stability of many commercially available alpha-amylases is reduced at a pH of less than about 4.0.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hrs, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch maybe further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation co-products such as distiller's dried grains (DDG) and distiller's dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Pulp and Paper Production

The alpha-amylase variants may also be used in the production of lignocellulosic materials, such as pulp, paper and cardboard, from starch reinforced waste paper and cardboard, especially where re-pulping occurs at pH above 7 and where amylases facilitate the disintegration of the waste material through degradation of the reinforcing starch. The alpha-amylase variants are especially useful in a process for producing a papermaking pulp from starch-coated printed-paper. The process may be performed as described in WO 95/14807, comprising the following steps:

a) disintegrating the paper to produce a pulp,
b) treating with a starch-degrading enzyme before, during or after step a), and
c) separating ink particles from the pulp after steps a) and b).

The alpha-amylase variants may also be useful in modifying starch where enzymatically modified starch is used in papermaking together with alkaline fillers such as calcium carbonate, kaolin and clays. With the alpha-amylase variants it is possible to modify the starch in the presence of the filler thus allowing for a simpler integrated process.

Desizing of Textiles, Fabrics and Garments

The alpha-amylase variants may also be very useful in textile, fabric or garment desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing process is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size leads to some fiber damage because of the rather aggressive chemicals used. Accordingly, it would be desirable to use the alpha-amylase variants as they have an improved performance in alkaline solutions. The alpha-amylase variants may be used alone or in combination with a cellulase when desizing cellulose-containing fabric or textile.

Desizing and bleaching processes are well known in the art. For instance, such processes are described in, e.g., WO 95/21247, U.S. Pat. No. 4,643,736, EP 119920, which are hereby incorporated by reference.

Cleaning Processes and Detergent Compositions

The alpha-amylase variants may be added as a component of a detergent composition for various cleaning or washing processes, including laundry and dishwashing. For example, the variants may be used in the detergent compositions described in WO 96/23874 and WO 97/07202.

The alpha-amylase variants may be incorporated in detergents at conventionally employed concentrations. For example, a variant of the invention may be incorporated in an amount corresponding to 0.00001-10 mg (calculated as pure, active enzyme protein) of alpha-amylase per liter of wash/dishwash liquor using conventional dosing levels of detergent.

The detergent composition may for example be formulated as a hand or machine laundry detergent composition, including a laundry additive composition suitable for pretreatment of stained fabrics and a rinse added fabric softener composition or be formulated as a detergent composition for use in general household hard surface cleaning operations, or be formulated for hand or machine dishwashing operations.

The detergent composition may further comprise one or more other enzymes, such as a lipase, peroxidase, protease, another amylolytic enzyme, e.g., another alpha-amylase, glucoamylase, maltogenic amylase, CGTase, cellulase, mannanase (such as Mannaway™ from Novozymes, Denmark)), pectinase, pectin lyase, cutinase, and/or laccase.

In general the properties of the chosen enzyme(s) should be compatible with the selected detergent (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive, e.g., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols, fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition may be in any convenient form, e.g., a bar, a tablet, a powder, a granule, a paste or a liquid. A liquid detergent may be aqueous, typically containing up to about 70% water and 0 to about 30% organic solvent, or non-aqueous.

The detergent composition comprises one or more surfactants, which may be non-ionic including semi-polar and/or anionic and/or cationic and/or zwitterionic. The surfactants are typically present at a level of from about 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0 to about 65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxy acids of, e.g., the amide, imide, or sulfone type.

The enzyme(s) of the detergent composition may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19708 and WO 92/19709.

The detergent may also contain other conventional detergent ingredients such as, e.g., fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The detergent compositions may comprise any enzyme in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor. One or more of the variant enzymes described herein may additionally be incorporated in the detergent formulations disclosed in WO 97/07202, which is hereby incorporated as reference.

This disclosure includes further detail in the following examples, which are not in any way intended to limit the scope of what is claimed. The following examples are thus offered to illustrate, but not to limit what is claimed.

EXAMPLES

Materials

Enzymes
SP722: SEQ ID NO: 10, available from Novozymes, and disclosed in WO 95/26397.
AA560: SEQ ID NO: 2; disclosed in WO 00/60060 and available from Novozymes A/S; disclosed in Danish patent application no. PA 1999 00490; deposited on Jan. 25, 1999 at DSMZ and assigned the DSMZ no. 12649.
Bacillus subtilis SHA273: see WO 95/10603
Methods
General Molecular Biology Methods
Unless otherwise mentioned the DNA manipulations and transformations were performed using standard methods of molecular biology (Sambrook et al. (1989); Ausubel et al. (1995); Harwood and Cutting (1990)).
Fermentation of Alpha-Amylases and Variants
Fermentation may be performed by methods well known in the art or as follows.

A B. subtilis strain harboring the relevant expression plasmid is streaked on a LB-agar plate with a relevant antibiotic, and grown overnight at 37° C.

The colonies are transferred to 100 ml BPX media supplemented with a relevant antibiotic (for instance 10 mg/l chloroamphinicol) in a 500 ml shaking flask.
Composition of BPX medium:
Potato starch 100 g/l
Barley flour 50 g/l
BAN 5000 SKB 0.1 g/l
Sodium caseinate 10 g/l
Soy Bean Meal 20 g/l
$Na_2HPO_4$, 12 $H_2O$ 9 g/l
Pluronic™ 0.1 g/l The culture is shaken at 37° C. at 270 rpm for 4 to 5 days.
Cells and cell debris are removed from the fermentation broth by centrifugation at 4500 rpm in 20-25 minutes. Afterwards the supernatant is filtered to obtain a completely clear solution. The filtrate is concentrated and washed on an UF-filter (10000 cut off membrane) and the buffer is changed to 20 mM acetate pH 5.5. The UF-filtrate is applied on an S-sepharose F.F. and elution is carried out by step elution with 0.2 M NaCl in the same buffer. The eluate is dialysed against 10 mM Tris, pH 9.0 and applied on a Q-sepharose F.F. and eluted with a linear gradient from 0-0.3 M NaCl over 6 column volumes. The fractions, which contain the activity (measured by the Phadebas assay) are pooled, pH was adjusted to pH 7.5 and remaining color was removed by a treatment with 0.5% w/vol. active coal in 5 minutes.
Determination of Residual Activity at pH 4.0
Reagents etc.
Buffer: 50 mM Citrate, pH 4, 0.05% Triton-X100
Prepare 500 ml stock solution.
Stability buffer: 50 mM Carbonate buffer ($NaHCO_3$), pH 8, 1 mM $CaCl_2$, 0.05% Triton-X100

Sample Preparation
Samples are centrifuged at 20,000 rpm for 2 minutes. If necessary the samples may be diluted in a stability buffer.
Incubation
100 microliters prepared sample
Ad 1000 microliters buffer
Incubate at 35° C. and withdraw 20 microliters aliquots in a 200 microliters cold stability buffer after 0, 20 and 48 hours. These can be stored on ice for later activity determination.
Assay
Measure the residual activity using the Phabedas assay, see protocol below.
Measurement of the Calcium- and pH-Dependent Stability
Normally industrial liquefaction processes runs using pH 6.0-6.2 as liquefaction pH and an addition of 40 ppm free calcium in order to improve the stability at 95° C.-105° C. Some of the herein proposed substitutions have been made in order to improve the stability at
1. pH lower than pH 6.2 and/or
2. free calcium levels lower than 40 ppm.

Two different methods can be used to measure the alterations in stability obtained by the different substitutions in the alpha-amylase in question:
Method 1. One assay which measures the stability at reduced pH, pH 5.0, in the presence of 5 ppm free calcium.
10 micro g of the variant are incubated under the following conditions: A 0.1 M acetate solution, pH adjusted to pH 5.0, containing 5 ppm calcium and 5% w/w common corn starch (free of calcium). Incubation is made in a water bath at 95° C. for 30 minutes.
Method 2. One assay, which measure the stability in the absence of free calcium and where the pH is maintained at pH 6.0. This assay measures the decrease in calcium sensitivity: 10 micro g of the variant were incubated under the following conditions: A 0.1 M acetate solution, pH adjusted to pH 6.0, containing 5% w/w common corn starch (free of calcium). Incubation was made in a water bath at 95° C. for 30 minutes.
Assays for Alpha-Amylase Activity
1. Phadebas Assay
Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

2. Alternative Method

Alpha-amylase activity is determined by a method employing the PNP-G7 substrate. PNP-G7 which is a abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at $\lambda=405$ nm (400-420 nm). Kits containing PNP-G7 substrate and alpha-Glucosidase is manufactured by Boehringer-Mannheim (cat. no. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-Glucosidase solution with 1 ml substrate.

The assay is performed by transforming 20 microliters enzyme solution to a 96 well microtitre plate and incubating at 25° C. 200 microliters working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question under the given set of conditions.

3. Enzchek® Amylase Activity Assay

Alpha-amylase activity may also be determined by a method employing the EnzChek® substrate. The substrate in the EnzChek® Ultra Amylase Assay Kit (E33651, Invitrogen, La Jolla, Calif., USA) is a corn starch derivative, DQ™ starch, which is corn starch labeled with BODIPY® FL dye to such a degree that fluorescence is quenched.

One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.12 mM $CaCl_2$, pH 5.5 is added, vortexed thoroughly and stored at room temperature, in the dark until ready to use. The substrate working solution is prepared by diluting 10-fold in residual activity buffer (100 mM acetate, 0.01% (w/v) TRITON® X100, 0.12 mM $CaCl_2$, pH 5.5) giving a substrate concentration of 100 micrograms/ml. Immediately after incubation the enzyme is diluted to a concentration of 20 ng enzyme protein/mL in 100 mM acetate, 0.01% (W/v) TRITON® X100, 0.12 mM $CaCl_2$, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Example 1

Preparation of Variants

Using the parent alpha-amylase AA560+delta(D183+G184)+N195F+R118K+R320K+R458K (disclosed in WO 01/66712) following variants were constructed:

1. D163Q+D188N+M208F+D209S+K242P+S244W;
2. D163N+R181A+G182A+K185T+G186N+D188N+D205N+M208F+D209S+V238I+K242P+S244W;
3. N128W+D163N+R181A+G182N+K185T+G186N+D188N+D205N+M208F+D209S+K242P+S244W;
4. D163N+R181A+G182N+K185T+G186N+D188N+D205N+M208F+D209S+K242P+S244W+N409D+D432N+A434P;
5. D163N+R181A+G182N+K185T+G186N+D188N+D205N+M208F+D209S+K242P+S244W

Example 2

Measurement of Residual Activity at pH 4.0

The residual activity at pH 4.0 was measured for the parent amylase and 5 variants prepared in example 1. All measurements were done as double determinations. The results are expressed in percent of the initial activity.

The following results were obtained demonstrating the improved stability of the variants of the invention at pH 4.0:

|  | 0 hours | 20 hours | 48 hours |
|---|---|---|---|
| Parent alpha-amylase | 100% | 35% | 25% |
| variant 1 | 100% | 65% | 34% |
| variant 2 | 100% | 80% | 70% |
| variant 3 | 100% | 87% | 85% |
| variant 4 | 100% | 88% | 84% |
| variant 5 | 100% | 97% | 96% |

Example 3

Residual Activity after Incubation with Strong Chelators

The parent alpha-amylase and variant 5 described in example 1 was incubated in the presence of strong chelators.

For incubation with chelators following mixtures were prepared:

100 microliters 250 mM EDTA or 100 microliters 10% DTPA
100 microliters enzyme preparation
Ad 1000 microliters with buffer.

Samples were incubated at 35° C. for 18 hours and the activity was determined using the PNP-G7 method described above.

|  | Parent | Variant 5 |
|---|---|---|
| DTPA | 6% | 42% |
| EDTA | 15% | 79% |

The results clearly show that the variant of the invention is considerably more resistant to the presence of strong chelators than the parent alpha-amylase.

Example 4

Measurement of Residual Activity at pH 3.0

Variant 5 and the parent alpha-amylase described in example 1 were incubated at pH 3.0 at 35° C. for 18 hours and the residual activity was determined using the PNP-G7 assay described above.

|       | Parent | Variant 5 |
|-------|--------|-----------|
| pH 3  | 1%     | 79%       |

The results show the variant of the invention also 0 has improved stability at pH 3. compared with the parent alpha-amylase.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention is further defined in the following paragraphs:

Paragraph 1. An isolated variant alpha-amylase, comprising two or more alterations at positions corresponding to positions 163, 188, 205, 208, and 209 of the mature polypeptide of SEQ ID NO: 2, wherein
 (a) the variant has a sequence identity to any of SEQ ID NOS: 2, 4, 6, 8, 10, 11, 12, 13, 14, 15, 16, and 17 of at least 70% and less than 100%.
 (b) each alteration is independently a substitution, deletion or insertion; and
 (c) the variant has alpha-amylase activity.

Paragraph 2. The variant of paragraph 1, which has at least 80% sequence identity to sequence identity to any of SEQ ID NOS: 2, 4, 6, 8, 10, 11, 12, 13, 14, 15, 16, and 17.

Paragraph 3. The variant of paragraph 1, which at least 90% sequence identity to sequence identity to any of SEQ ID NOS: 2, 4, 6, 8, 10, 11, 12, 13, 14, 15, 16, and 17.

Paragraph 4. The variant of paragraph 1, which at least 95% sequence identity to sequence identity to any of SEQ ID NOS: 2, 4, 6, 8, 10, 11, 12, 13, 14, 15, 16, and 17.

Paragraph 5. The variant of any of paragraphs 1-4, which wherein the alterations at positions 163, 188, 205, 208, and 209 are substitutions.

Paragraph 6. The variant of any of paragraphs 1-4, which comprises a substitution at the positions corresponding to positions 163 and 188.

Paragraph 7. The variant of any of paragraphs 1-4, which comprises a substitution at the positions corresponding to positions 163 and 205.

Paragraph 8. The variant of any of paragraphs 1-4, which comprises a substitution at the positions corresponding to positions 163 and 208.

Paragraph 9. The variant of any of paragraphs 1-4, which comprises a substitution at the positions corresponding to positions 163 and 209.

Paragraph 10. The variant of any of paragraphs 1-4, which comprises a substitution at the positions corresponding to positions 188 and 205.

Paragraph 11. The variant of any of paragraphs 1-4, which comprises a substitution at the positions corresponding to positions 188 and 208.

Paragraph 12. The variant of any of paragraphs 1-4, which comprises a substitution at the positions corresponding to positions 188 and 209.

Paragraph 13. The variant of any of paragraphs 1-4, which comprises a substitution at the positions corresponding to positions 205 and 208.

Paragraph 14. The variant of any of paragraphs 1-4, which comprises a substitution at the positions corresponding to positions 205 and 209.

Paragraph 15. The variant of any of paragraphs 1-4, which comprises a substitution at the positions corresponding to positions 208 and 209.

Paragraph 16. The variant of any of paragraphs 1-4, which comprises a substitution at the positions corresponding to positions 163, 188, and 205.

Paragraph 17. The variant of any of paragraphs 1-4, which comprises a substitution at the positions corresponding to positions 163, 188, and 208.

Paragraph 18. The variant of any of paragraphs 1-4, which comprises a substitution at the positions corresponding to positions 163, 188, and 209.

Paragraph 19. The variant of any of paragraphs 1-4, which comprises a substitution at the positions corresponding to positions 188, 205, and 208.

Paragraph 20. The variant of any of paragraphs 1-4, which comprises a substitution at the positions corresponding to positions 188, 205, and 209.

Paragraph 21. The variant of any of paragraphs 1-4, which comprises a substitution at the positions corresponding to positions 205, 208, and 209.

Paragraph 22. The variant of any of paragraphs 1-4, which comprises a substitution at the positions corresponding to positions 163, 188, 205, and 208.

Paragraph 23. The variant of any of paragraphs 1-4, which comprises a substitution at the positions corresponding to positions 163, 188, 205, and 209.

Paragraph 24. The variant of any of paragraphs 1-4, which comprises a substitution at the positions corresponding to positions 188, 205, 208, and 209.

Paragraph 25. The variant of any of paragraphs 1-4, which comprises a substitution at the positions corresponding to positions 163, 188, 205, 208, and 209.

Paragraph 26. The variant of any of paragraphs 1-25, wherein the alterations are selected among: X163Q,N, X188N, X205N, X208Y and X209N,S.

Paragraph 27. The variant of any of paragraphs 1-26, further comprising one or more alterations selected from the group consisting of a deletion at a position corresponding to positions 183 and 184 and a substitution at a position corresponding to the positions selected from the group consisting of 186, 193, 195, 202, 206, 214, 244, 452, 474 and 475

Paragraph 28. The variant of any of paragraphs 1-27, which further comprises one or more alterations selected from the group of X181*+X182*, X182*+X183*, X183*+X184*, X185K, X167W, X202L/I/T, X203Y, X167W+X168E+X169E+X170R, X51T+X109G+X203Y, X109G+X203Y, X189W, X189W+x190E+x193T, X190E, X193T, X303K, X303K+x305R+x306D+X409N+X432N+X434D, X305R, X306D, X409N, X432N, X434D.

Paragraph 29. The variant of any of paragraphs 1-28, which further comprises one or more alterations selected from the group consisting of A113E, N116V, V117F, L118K, A119V, V120I, N123D, N126D, N128T, Q129K, G133E, D134P, Y135F, T136E, A139G, D144T, N150D, T151Q, D154S, R158N, W159S, Y160E, V165T, W167F, Q169A, S170K, R171G, Q172*, F173E, Q174R, N175T, R176G, I177V, Y178F, K179R, F180I, R181A, D183E, G184N, A186K, W189E, E190N, S193T/D, N195F, Y203F, V206I, E212D, V214R, and N215R.

Paragraph 30. The variant of any of paragraphs 1-29, which further comprises one or more alterations selected from the group consisting of D183*+G184*, G186A,Y,T, T193F, N195F, M202L,I,T,S,A, I206F,Y, V214I, S244A,D,E,N,Q, W, T452HY, G474R, G475R.

Paragraph 31. The variant of any of paragraphs 1-30 selected from the group consisting of:
D188N+D209S;
D163N+D188N+D209S;
D163N+D188N+D205N+D209S;
D163N+D188N+D205N+M208F+D209S;
D207N+D209S;
D163N+D207N+D209S;
D163N+D188N+D207N+D209S;
D163N+D188N+D199N+D207N+D209S;
D163N+D188N+D199N+D205N+D207N+D209S;
D163N+D188N+D199N+D205N+M208F+D207N+D209S;
D163N+R181A+G182N+G186N+D188N+D205N+D209S;
D163N+R181A+G182N+K185T+G186N+D188N+D205N+D209S;
D163N+R181A+G182N+K185T+G186N+D188N+D205N+M208F+D209S;
D163N+R181A+G182N+D188N+D199N+D205N+M208F+D207N+D209S;
D163N+R181A+G182N+K185T+D188N+D199N+D205N+M208F+D207N+D209S;
D163N+R181A+G182N+K185T+G186N+D188N+D199N+D205N+M208F+D207N+D209S;
D163N+R181A+G182N+K185T+G186N+D188N+D205N+M208F+D209S+K242P+S244W;
D163N+R181A+G182N+K185T+G186N+D188N+D205N+M208F+D209S+K242P+S244W+N409D+D432N+A434P;
D163N+R181A+G182N+K185T+G186N+D188N+D205N+M208F+D209S+K242P+S244W+H408W+N409D+D432N+A434P;
N128W+D163N+R181A+G182N+K185T+G186N+D188N+D205N+M208F+D209S+K242P+S244W;
D163N+R181A+G182N+K185T+G186N+D188N+D205N+M208F+D209S+V238I+K242P+S244W; and
D163Q+D188N+M208F+D209S+K242P+S244W.

Paragraph 32. The variant of any of paragraphs 1-31 selected from the group consisting of:
D188N+D209S
D163N+D188N+D209S
D163N+D188N+D205N+D209S
D163N+D188N+D205N+M208F+D209S
D207N+D209S
D163N+D207N+D209S
D163N+D188N+D207N+D209S
D163N+D188N+D199N+D207N+D209S
D163N+D188N+D199N+D205N+D207N+D209S
D163N+D188N+D199N+D205N+M208F+D207N+D209S
D163N+R181A+G182N+G186N+D188N+D205N+D209S
D163N+R181A+G182N+K185T+A186N+D188N+D205N+D209S
D163N+R181A+G182N+K185T+A186N+D188N+D205N+M208F+D209S
D163N+R181A+G182N+D188N+D199N+D205N+M208F+D207N+D209S
D163N+R181A+G182N+K185T+D188N+D199N+D205N+M208F+D207N+D209S
D163N+R181A+G182N+K185T+A186N+D188N+D199N+D205N+M208F+D207N+D209S.

Paragraph 33. The variant of any of paragraphs 1-32 selected from the group consisting of:
D207N+D186N
D207N+D186N+D162N
D207N+D186N+D162N+D203N
D207N+D186N+D162N+D203N+M206Y
D207N+D186N+D162N+D203N+M206Y+D105N
D207N+A184K+T187E
D207N+A184K+T187E+D186N
D207N+A184K+T187E+D186N+D162N
D207N+A184K+T187E+D186N+D162N+D203N
D207N+A184K+T187E+D186N+D162N+D203N+M206Y
D207N+A184K+T187E+D186N+D162N+D203N+M206Y+D105N.

Paragraph 34. A detergent composition comprising a variant of any of paragraphs 1-33 and a surfactant.

Paragraph 35. A composition comprising a variant of any of paragraphs 1-33 and one or more enzymes selected from the group consisting of beta-amylase, cellulase (beta-glucosidase, cellobiohydrolase, and endoglucanase) glucoamylase, hemicellulase (e.g., xylanase), isoamylase, isomerase, lipase, phytase, protease, and pullulanase.

Paragraph 36. Use of a variant of any of paragraphs 1-33 for washing and/or dishwashing.

Paragraph 37. Use of a variant of any of paragraphs 1-33 for desizing a textile.

Paragraph 38. Use of a variant of any of paragraphs 1-33 for producing a baked product.

Paragraph 39. Use of a variant of any of paragraphs 1-33 for liquefying a starch-containing material.

Paragraph 40. A method of producing liquefied starch, comprising liquefying a starch-containing material with a variant of any of paragraphs 1-33

Paragraph 41. A process of producing a fermentation product, comprising
(a) liquefying a starch-containing material with a variant of any of paragraphs 1-33 to produce a liquefied mash;
(b) saccharifying the liquefied mash to produce fermentable sugars; and
(c) fermenting the fermentable sugars in the presence of a fermenting organism.

Paragraph 42. The process of paragraph 41 wherein the starch-containing material is liquefied with the variant and a pullulanase, e.g., a GH57 pullulanase.

Paragraph 43. The process of paragraph 42 wherein the pullulanase is obtained from a strain of *Thermococcus*, including *Thermococcus* sp. AM4, *Thermococcus* sp. HJ21, *Thermococcus barophilus*, *Thermococcus gammatolerans*, *Thermococcus hydrothermalis*; *Thermococcus kodakarensis*, *Thermococcus litoralis*, and *Thermococcus onnurineus*; or from a strain of *Pyrococcus*, such as *Pyrococcus abyssi* and *Pyrococcus furiosus*.

Paragraph 44. The process of any of paragraphs 41-43 further comprising adding a protease, such as an acid fungal protease or a metalloprotease before, during and/or after liquefaction.

Paragraph 45. The process of paragraph 44, wherein the metalloprotease is obtained from a strain of *Thermoascus*, preferably a strain of *Thermoascus aurantiacus*, especially *Thermoascus aurantiacus* CGMCC No. 0670.

Paragraph 46. A process of producing a fermentation product, comprising contacting a starch substrate with a variant of any of paragraphs 1-33, a glucoamylase, and a fermenting organism.

Paragraph 47. The process of any of paragraphs 41-46, wherein the fermentation product is selected from the group consisting of alcohol (e.g., ethanol and butanol), organic acids (e.g., succinic acid and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

Paragraph 48. An isolated polynucleotide encoding the variant of any of paragraphs 1-33.

Paragraph 49. A nucleic acid construct comprising the polynucleotide of paragraph 48.

Paragraph 50. An expression vector comprising the nucleic acid construct of paragraph 49.

Paragraph 51. A host cell comprising the nucleic acid construct of paragraph 49.

Paragraph 52. A method of producing a variant, comprising:
  a. cultivating the host cell of paragraph 51 under conditions suitable for the expression of the alpha-amylase; and
  b. recovering the variant from the cultivation medium.

Paragraph 53. A transgenic plant, plant part or plant cell transformed with the polynucleotide of paragraph 48.

Paragraph 54. A method for preparing a variant of a parent alpha-amylase comprising the following steps:
  a. providing a nucleic acid encoding a parent alpha-amylase,
  b. introducing alterations in the nucleic acid sequence resulting in alterations of the encoded amino acid residues in two, three, four or five positions, said positions corresponding to positions in the parent alpha-amylase selected from the group consisting of 163, 188, 205, 208 and 209; the alteration(s) are independently
    (i) an insertion of an amino acid immediately downstream of the position,
    (ii) a deletion of the amino acid which occupies the position, and/or
    (iii) a substitution of the amino acid which occupies the position,
  c. optionally introducing further alterations in the nucleic acid sequence resulting in alterations of one or more amino acid residues in the B-domain of the parent alpha-amylase to the corresponding amino acid residue(s) in SEQ ID NO: 9;
  d. optionally introducing further alterations in the nucleic acid sequence resulting in alterations of the encoded amino acid residues selected from the group of X183*+X184*, X186A,Y,T, X193F, X195F, M202L,I,T,S,A, X206F,Y, X214I, X244A,D,E,N,Q,W, X452H,Y, X474R and X475R;
  e. expressing the altered nucleic acid sequence in a suitable host organism; and
  f. recovering the variant alpha-amylase,
wherein each position corresponds to a position of the amino acid sequence of the enzyme having the amino acid sequence of SEQ ID NO: 2.

Paragraph 55. The method of paragraph 54, wherein the alterations in b. are selected among: X163Q,N, X188N, X205N, X208Y and, X209N,S.

Paragraph 56. The method of paragraph 54 or 55, wherein the parent alpha-amylase is a Termamyl-like ampha-amylase.

Paragraph 57. The method of paragraph 56, wherein the parent alpha-amylase is selected among alpha-amylases having SEQ ID NO: 2, 4, 6, 8 or 10, or alpha-amylases derived from a strain of the *Bacillus* sp. NCIB 12289, NCIB 12512, NCIB 12513 or DSM 9375, and the #707 alpha-amylase described by Tsukamoto et al., 1988, *Biochemical and Biophysical Research Communications* 151: 25-31, or alpha-amylases having at least 70%, preferably at least 75%, more preferably at least 80%, more preferably at least 85%, even more preferably at least 90%, most preferably at least 95%, and even most preferably at least about 97% sequence identity to the amino acid sequence of one of these.

The invention claimed is:

1. An isolated variant alpha-amylase, comprising two or more alterations at positions corresponding to positions 163, 188, 205, 208, and 209 of the mature polypeptide of SEQ ID NO: 2, wherein
   (a) the variant has at least 90% and less than 100% sequence identity to SEQ ID NO:4;
   (b) each alteration is independently a substitution, deletion or insertion; and
   (c) the variant has alpha-amylase activity.

2. The variant of claim 1, which has at least 95% sequence identity to SEQ ID NO:4.

3. The variant of claim 1, wherein the alterations at positions 163, 188, 205, 208, and 209 are substitutions.

4. The variant of claim 1, wherein the alterations are selected among: X163Q,N, X188N, X205N, X208Y and X209N,S.

5. The variant of claim 1, further comprising one or more alterations selected from the group consisting of a deletion at a position corresponding to positions 183 and 184 and a substitution at a position corresponding to the positions selected from the group consisting of 186, 193, 195, 202, 206, 214, 244, 452, 474 and 475.

6. The variant of claim 1, which further comprises one or more alterations selected from the group of X181*+X182*, X182*+X183*, X183*+X184*, X185K, X167W, X202L/I/T, X203Y, X167W+X168E+X169E+X170R, X51T+X109G+X203Y, X109G+X203Y, X189W, X189W+x190E+x193T, X190E, X193T, X303K, X303K+x305R+x306D+X409N+X432N+X434D, X305R, X306D, X409N, X432N, X434D.

7. The variant of claim 1, which further comprises one or more alterations selected from the group consisting of A113E, N116V, V117F, L118K, A119V, V120I, N123D, N126D, N128T, Q129K, G133E, D134P, Y135F, T136E, A139G, D144T, N150D, T151Q, D154S, R158N, W159S, Y160E, V165T, W167F, Q169A, S170K, R171G, Q172*, F173E, Q174R, N175T, R176G, I177V, Y178F, K179R, F180I, R181A, D183E, G184N, A186K, W189E, E190N, S193T/D, N195F, Y203F, V206I, E212D, V214R, and N215R.

8. The variant of claim 1 selected from the group consisting of:
   D188N+D209S;
   D163N+D188N+D209S;
   D163N+D188N+D205N+D209S;
   D163N+D188N+D205N+M208F+D209S;
   D207N+D209S;
   D163N+D207N+D209S;
   D163N+D188N+D207N+D209S;
   D163N+D188N+D199N+D207N+D209S;
   D163N+D188N+D199N+D205N+D207N+D209S;
   D163N+D188N+D199N+D205N+M208F+D207N+D209S;
   D163N+R181A+G182N+G186N+D188N+D205N+D209S;
   D163N+R181A+G182N+K185T+G186N+D188N+D205N+D209S;
   D163N+R181A+G182N+K185T+G186N+D188N+D205N+M208F+D209S;

D163N+R181A+G182N+D188N+D199N+D205N+
  M208F+D207N+D209S;
D163N+R181A+G182N+K185T+D188N+D199N+
  D205N+M208F+D207N+D209S;
D163N+R181A+G182N+K185T+G186N+D188N+
  D199N+D205N+M208F+D207N+D209S;
D163N+R181A+G182N+K185T+G186N+D188N+
  D205N+M208F+D209S+K242P+S244W;
D163N+R181A+G182N+K185T+G186N+D188N+
  D205N+M208F+D209S+K242P+S244W+N409D+
  D432N+A434P;
D163N+R181A+G182N+K185T+G186N+D188N+
  D205N+M208F+D209S+K242P+S244W+H408W+
  N409D+D432N+A434P;
N128W+D163N+R181A+G182N+K185T+G186N+
  D188N+D205N+M208F+D209S+K242P+S244W;
D163N+R181A+G182N+K185T+G186N+D188N+
  D205N+M208F+D209S+V238I+K242P+S24 4W; and
D163Q+D188N+M208F+D209S+K242P+S244W.

9. The variant of claim 1 selected from the group consisting of:
D188N+D209S
D163N+D188N+D209S
D163N+D188N+D205N+D209S
D163N+D188N+D205N+M208F+D209S
D207N+D209S
D163N+D207N+D209S
D163N+D188N+D207N+D209S
D163N+D188N+D199N+D207N+D209S
D163N+D188N+D199N+D205N+D207N+D209S
D163N+D188N+D199N+D205N+M208F+D207N+
  D209S
D163N+R181A+G182N+G186N+D188N+D205N+
  D209S
D163N+R181A+G182N+K185T+A186N+D188N+
  D205N+D209S
D163N+R181A+G182N+K185T+A186N+D188N+
  D205N+M208F+D209S
D163N+R181A+G182N+D188N+D199N+D205N+
  M208F+D207N+D209S
D163N+R181A+G182N+K185T+D188N+D199N+
  D205N+M208F+D207N+D209S
D163N+R181A+G182N+K185T+A186N+D188N+
  D199N+D205N+M208F+D207N+D209S.

10. The variant of claim 1 selected from the group consisting of:
D207N+D186N
D207N+D186N+D162N
D207N+D186N+D162N+D203N
D207N+D186N+D162N+D203N+M206Y
D207N+D186N+D162N+D203N+M206Y+D105N
D207N+A184K+T187E
D207N+A184K+T187E+D186N
D207N+A184K+T187E+D186N+D162N
D207N+A184K+T187E+D186N+D162N+D203N
D207N+A184K+T187E+D186N+D162N+D203N+
  M206Y
D207N+A184K+T187E+D186N+D162N+D203N+
  M206Y+D105N.

11. A detergent composition comprising a variant of claim 1 and a surfactant.

12. A method of producing liquefied starch, comprising liquefying a starch-containing material with a variant of claim 1.

13. A process of producing a fermentation product, comprising
  a. liquefying a starch-containing material with a variant of claim 1 to produce a liquefied mash;
  b. saccharifying the liquefied mash to produce fermentable sugars; and
  c. fermenting the fermentable sugars in the presence of a fermenting organism.

14. A process of producing a fermentation product, comprising contacting a starch substrate with a variant of claim 1, a glucoamylase, and a fermenting organism.

* * * * *